(12) United States Patent
Nahavandi et al.

(10) Patent No.: US 11,666,498 B2
(45) Date of Patent: Jun. 6, 2023

(54) PATIENT SUPPORT APPARATUS WITH EQUIPMENT WEIGHT LOG

(71) Applicant: Stryker Corporation, Kalamazoo, MI (US)

(72) Inventors: Kurosh Nahavandi, Portage, MI (US); David Buick, Portage, MI (US); Placide Nibakuze, Kalamazoo, MI (US); Sujay Sukumaran, Portage, MI (US); Celso Henrique Farnese Pires Pereira, Portage, MI (US); Ian Christopher Geiman, South Lyon, MI (US)

(73) Assignee: Stryker Corporation, Kalamazoo, MI (US)

( * ) Notice: Subject to any disclaimer, the term of this patent is extended or adjusted under 35 U.S.C. 154(b) by 323 days.

(21) Appl. No.: 16/992,515

(22) Filed: Aug. 13, 2020

(65) Prior Publication Data
US 2021/0045951 A1 Feb. 18, 2021

Related U.S. Application Data

(60) Provisional application No. 62/885,954, filed on Aug. 13, 2019.

(51) Int. Cl.
*A61G 7/05* (2006.01)

(52) U.S. Cl.
CPC ........ *A61G 7/0527* (2016.11); *A61G 2203/16* (2013.01); *A61G 2203/20* (2013.01); *A61G 2203/32* (2013.01)

(58) Field of Classification Search
CPC ............. A61G 7/0527; A61G 2203/16; A61G 2203/20; A61G 2203/32; A61G 7/05; A61G 2203/44; A61B 5/1115
See application file for complete search history.

(56) References Cited

U.S. PATENT DOCUMENTS 10,054,479 B2   8/2018  Nachtigal et al.
2008/0235872 A1* 10/2008 Newkirk .............. A61G 7/0524
                                                         5/658

(Continued)

OTHER PUBLICATIONS

Stryker Operations Manual, S3 MedSurg Bed with StayPut Frame, Model 3005, Mar. 2012.

(Continued)

*Primary Examiner* — Fredrick C Conley
(74) *Attorney, Agent, or Firm* — Warner Norcross + Judd LLP

(57) ABSTRACT

A patient support apparatus, such as a bed, cot, stretcher, or the like, includes a litter frame, a support deck, a plurality of force sensors adapted to output signals corresponding to downward forces exerted on the support deck, and a controller configured carrying out various functions and to display various screens on a touchscreen or display, including a scale home screen and a scale equipment screen. A patient's current weight can be displayed on the scale home screen and the weight of equipment supported on the apparatus can be displayed on the scale home screen and the scale equipment screen. When a patient's current weight is characterized as possibly including non-patient weight, the controller can display a warning screen.

19 Claims, 19 Drawing Sheets

(56) References Cited

U.S. PATENT DOCUMENTS

| | | |
|---|---|---|
| 2014/0266733 A1* | 9/2014 | Hayes ............... A61G 7/05 |
| | | 600/484 |
| 2016/0022218 A1 | 1/2016 | Hayes et al. |
| 2016/0106345 A1 | 4/2016 | Kostic et al. |
| 2018/0153753 A1 | 6/2018 | Kostic et al. |
| 2019/0008708 A1 | 1/2019 | Moreno et al. |
| 2019/0336367 A1 | 11/2019 | Zerhusen et al. |

OTHER PUBLICATIONS

Stryker Operations Manual InTouch Critical Care Bed Model FL27, Apr. 2012.
Stryker Operations Manual Epic II Critical Care Bed, Model 2030, Jan. 2010.
Stryker Patient Care Maintenance Manual Modular Patient System (MPS) 3000 Bed, Mar. 1994.

\* cited by examiner

PATIENT SUPPORT APPARATUS WITH EQUIPMENT WEIGHT LOG

CROSS-REFERENCE TO RELATED APPLICATIONS

This application claims the benefit of U.S. provisional patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosure of which is incorporated herein by reference.

BACKGROUND

The present disclosure relates to patient support apparatuses, such as beds, cots, stretchers, operating tables, recliners, or the like.

Conventional patient support apparatuses comprise a base, a litter frame, a support deck on the litter frame upon which the patient is supported, and a scale system for determining the weight of a patient supported on the patient support apparatus. Control of the scale system is performed via a user interface provided on a footboard or on one or more of the side rails of the patient support apparatus. Often, operation of the user interface is complex, making the user interface difficult to operate. Patient weight is typically repeatedly monitored throughout care and treatment, adding to the burden placed on the operator of the user interface. Adding to this difficultly is the need to distinguish reliably between patient weight and non-patient weight from other loads supported on the patient support apparatus, such as medical equipment, pillows, blankets, etc.

SUMMARY

According to various embodiments, an improved patient support apparatus is provided that includes a plurality of force sensors. In its various embodiments, the present disclosure provides a patient support apparatus which reliably distinguishes between the weight of a patient and the weight of equipment or other objects on the apparatus. Through a touchscreen or other user interface of the patient support apparatus, a user can take an accurate patient's weight reading and log equipment or other non-patient weight added to or removed from the patient support apparatus. These and/or other features are disclosed in the various embodiments discussed herein.

According to one embodiment of the present disclosure, a patient support apparatus is provided that includes a litter frame, a support deck, a plurality of force sensors adapted to output signals corresponding to downward forces exerted on the support deck, a touchscreen, and a controller in operative communication with the plurality of force sensors and the touchscreen. The controller is configured to display a scale equipment screen and scale home screen at the touchscreen. The scale equipment screen includes an equipment weight indicator comprising a first numeric value representing a total weight of equipment added to or removed from the support deck and an equipment number indicator comprising a second numeric value representing a total number of pieces of equipment on the support deck. The scale home screen includes an equipment icon including the first and second numeric values and a patient weight indicator comprising a third numeric value representative of a current weight of a patient supported by the support deck based on readings from the plurality of force sensors. The controller displays the scale equipment screen in response to user-selection of the equipment icon on the scale home screen.

According to another embodiment of the present disclosure, a patient support apparatus is provided that includes a litter frame, a support deck, a plurality of force sensors adapted to output signals corresponding to downward forces exerted on the support deck, a display, and a controller in operative communication with the plurality of force sensors. The controller is configured to receive the signals provided by the plurality of force sensors, analyze the signals to determine a weight of a load supported on the support deck and characterize the weight as being an accurate patient weight or as possibly including non-patient weight, display a scale home screen including a save weight control and a weight indicator comprising a numeric value representative of the weight, and, upon user-selection of the save weight control on the scale home screen, display a warning screen comprising a warning message if the weight as is characterized as possibly including non-patient weight.

According to yet another embodiment of the present disclosure, a patient support apparatus is provided that includes a litter frame, a support deck, a plurality of force sensors adapted to output signals corresponding to downward forces exerted on the support deck, a display, and a controller in operative communication with the plurality of force sensors. The controller is configured to receive the signals provided by the plurality of force sensors, analyze the signals to determine a weight of a load supported on the support deck and characterize the weight as being an accurate patient weight or as possibly including non-patient weight, and display a scale home screen. The scale home screen includes a save weight control, an equipment icon including a first numeric value representing a total weight of equipment added to or removed from the support deck and a second numeric value representing a total number of pieces of equipment on the support deck, and a weight indicator comprising a third numeric value representative of the weight. Upon user-selection of the equipment icon on the scale home screen, the controller is configured to display a scale equipment screen comprising an equipment weight indicator comprising the first numeric value and an equipment number indicator comprising the second numeric value. Upon user-selection of the save weight control on the scale home screen, the controller is configured to display a warning screen comprising a warning message if the weight as is characterized as possibly including non-patient weight.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
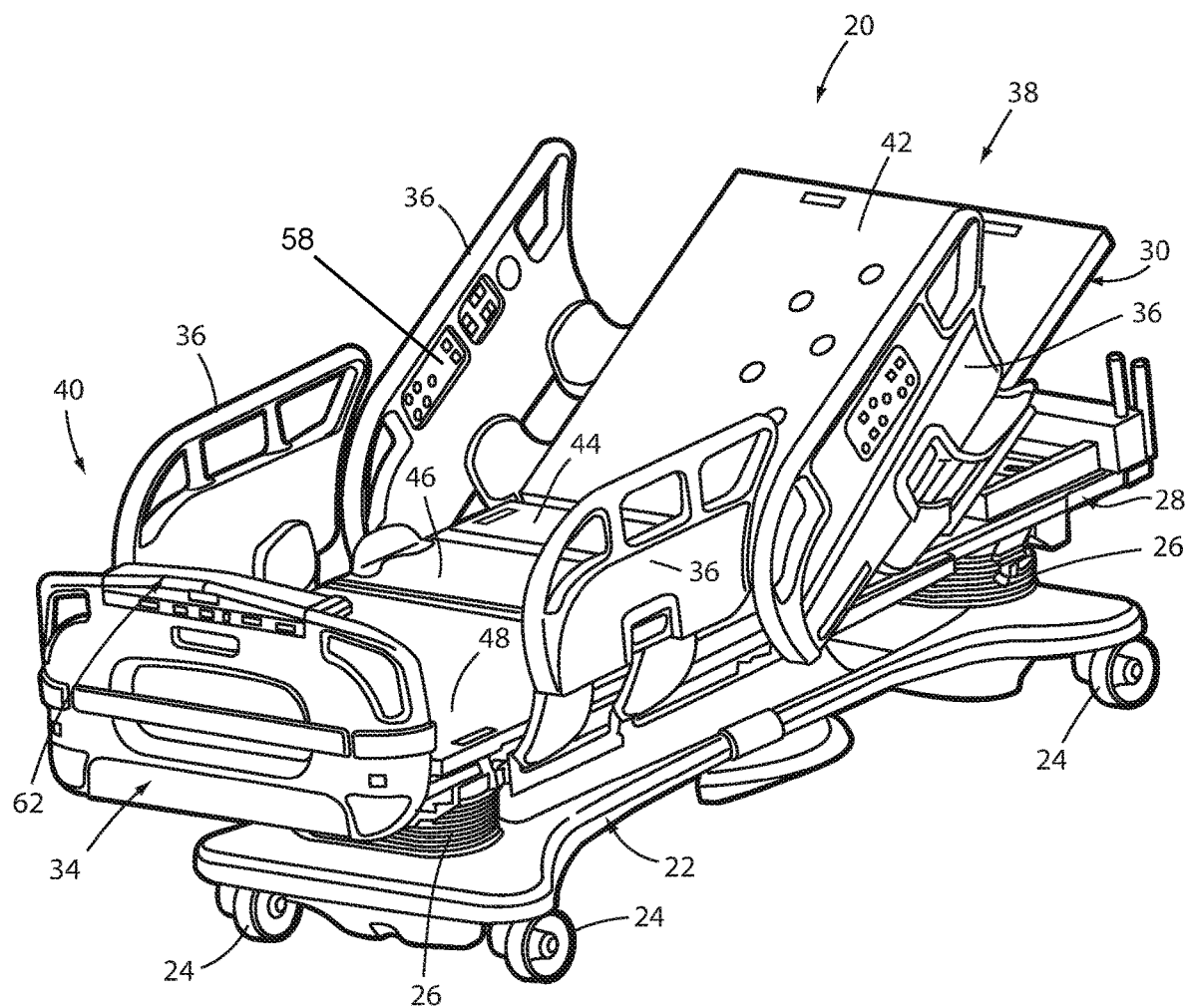
FIG. 1 is a perspective view of a patient support apparatus according to one embodiment of the disclosure.

An illustrative patient support apparatus 20 that incorporates one or more aspects of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a gurney, a recliner, an operating table, a residential bed, or any other structure capable of supporting a person, whether stationary or mobile and/or whether medical or residential.

In general, patient support apparatus 20 includes a base 22 having a plurality of wheels 24, a pair of lifts 26 supported on the base, a litter frame 28 supported on the lifts 26, and a support deck 30 supported on the litter frame 28. Patient support apparatus 20 further includes a headboard (not shown), a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36. In some embodiments, siderails 36 may be moved to one or more intermediate positions as well.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard, footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Figure 2:
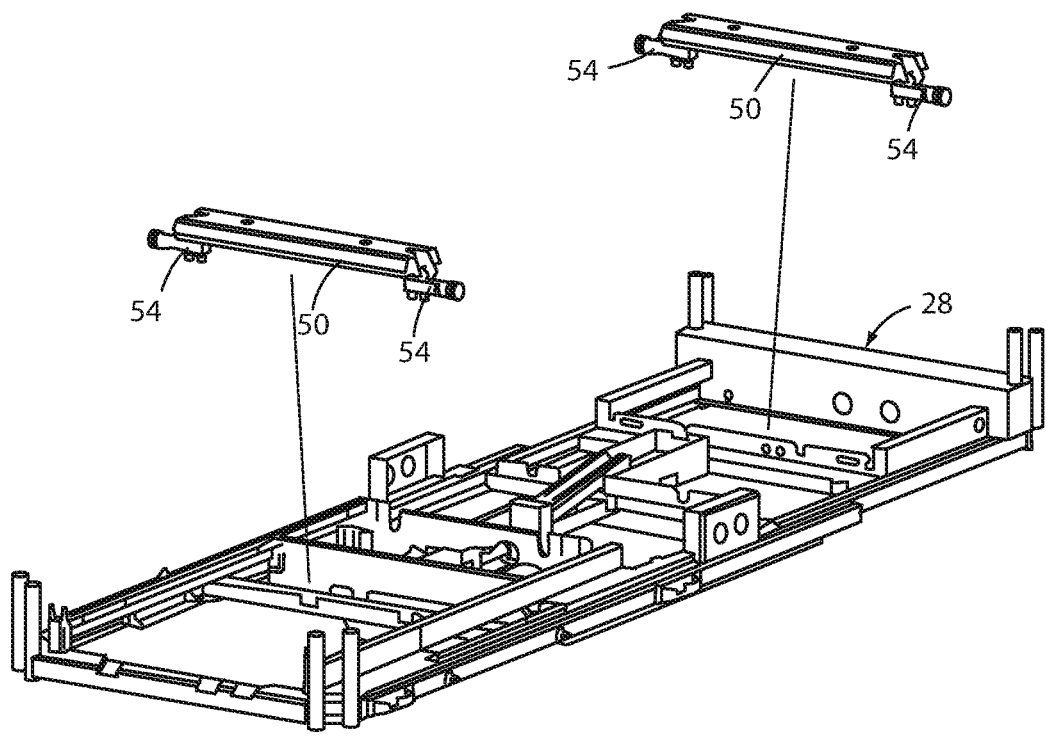
FIG. 2 is a perspective view of a litter frame of the patient support apparatus of FIG. 1.
Figure 3:
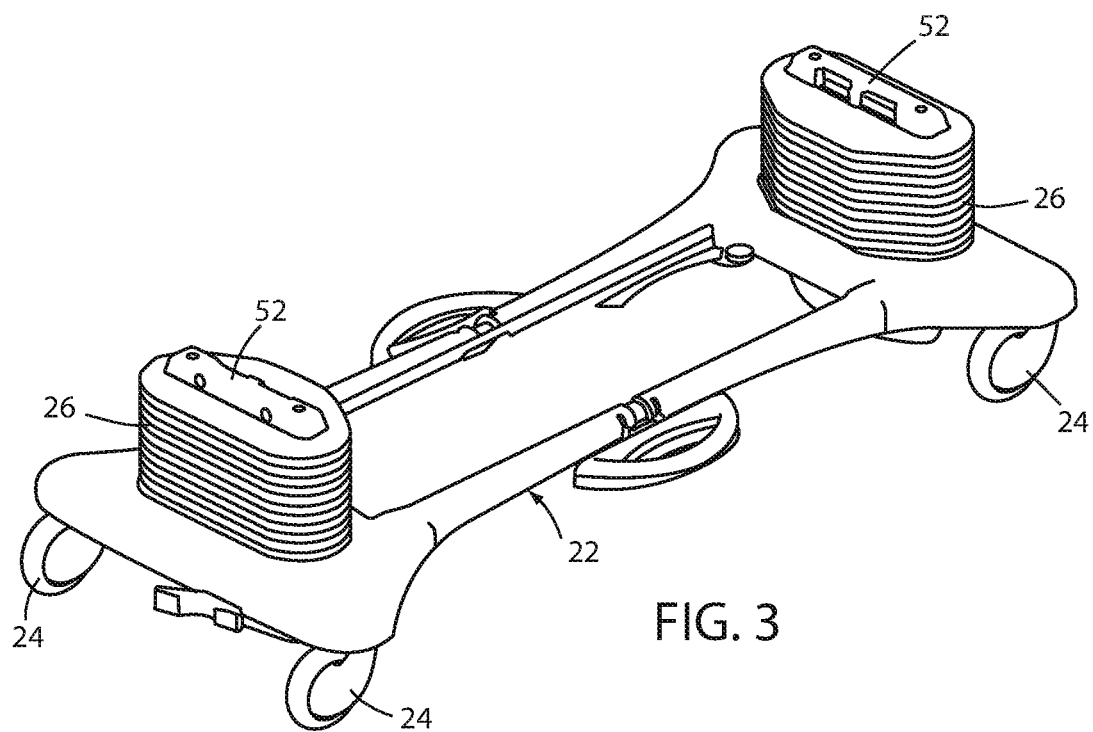
FIG. 3 is a perspective view of a base of the patient support apparatus of FIG. 1.

FIG. 2 illustrates in detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of force sensors 54, which may be load cells, or other types of force sensors, such as, but not limited to, linear variable displacement transducers and/or any one or more capacitive, inductive, and/or resistive transducers that are configured to produce a changing output in response to changes in the force exerted against them.

Although the illustrated embodiment of patient support apparatus 20 includes a total of four force sensors 54, it will be understood by those skilled in the art that different numbers of force sensors 54 may be used in accordance with the principles of the present disclosure. Force sensors 54 are configured to support litter frame 28. More specifically, force sensors 54 are configured such that they provide complete and exclusive mechanical support for litter frame 28 and all of the components that are supported on litter frame 28 (e.g. support deck 30, footboard 34, the headboard, siderails 36, etc.). Because of this construction, force sensors 54 are adapted to detect the weight of not only those components of patient support apparatus 20 that are supported by litter frame 28 (including litter frame 28 itself), but also any objects or persons who are wholly or partially being supported by support deck 30.

Force sensors 54 are adapted to detect downward forces exerted by an occupant of support deck 30. Thus, when an occupant is positioned on support deck 30 and substantially still (i.e. not moving in a manner involving accelerations that cause forces to be exerted against support deck 30), force sensors 54 will detect the weight of the occupant (as well as the weight of any equipment or non-occupant weight on the support deck 30, and any components of patient support apparatus 20 that are supported—directly or indirectly—by force sensors 54). Force sensors 54 can also be used to determine a center of gravity of the occupant in order to determine if the occupant is about to exit patient support apparatus 20. In alternative embodiments, the outputs from force sensors 54 are analyzed, not to determine a center of gravity, but instead to determine a weight distribution and/or a change in weight distribution, such as by determining one or more ratios of the relative weights sensed by the force sensors 54 and using them to determine if the occupant is about to exit patient support apparatus 20. In still other embodiments, force sensors 54 may be modified to detect forces other than, or in addition to, the downward forces exerted by the occupant. Other types of sensors may additionally or alternatively be used for determining the occupant's weight.

The outputs of force sensors 54 are part of a scale/exit detection system 56 that is used to detect the weight of an occupant of the patient support apparatus 20 and/or that is used as an exit detection system. The particular structural details of scale/exit detection system 56 can vary widely. When functioning as a scale system, the outputs of the force sensors 54 are read and a weight of the occupant is detected. When functioning as an exit detection system, the outputs of the force sensors 54 are read and used to detect when an occupant has exited the patient support apparatus 20, or when an occupant may be about to exit the patient support apparatus 20. Exemplary scale/exit detection systems are described in U.S. Patent Application Pub. No. 2017/0003159, filed by Kostic et al., entitled "PERSON SUPPORT APPARATUS WITH LOAD CELLS," and in U.S. Pat. No. 5,276,432, issued to Travis, entitled "PATIENT EXIT DETECTION MECHANISM FOR HOSPITAL BED," the complete disclosures of both of which are also hereby incorporated herein by reference. Other types of scale and/or exit detection systems may be used. It is also noted that while a combination scale and exit detection system 56 is discussed herein, in alternative embodiments, the system 56 can function as a scale system without exit detection functionality.

Referring to FIG. 1, patient support apparatus 20 further includes a plurality of user interfaces 58, 60, 62 that enable a user of patient support apparatus 20, such as a patient and/or an associated caregiver, to control one or more aspects of patient support apparatus 20, including the scale/exit detection system 56. In the embodiment shown in FIG. 1, patient support apparatus 20 includes a pair of inner siderail user interfaces 58 (only one of which is visible), a pair of outer siderail user interfaces 60 (only one of which is visible), and a footboard user interface 62. Footboard user interface 62 and outer siderail user interfaces 60 are intended to be used by caregivers, or other authorized personnel, while inner siderail user interfaces 58 are intended to be used by the patient associated with patient support apparatus 20. Not all of the user interfaces 58, 60, 62 include the same controls and/or functionality. In the illustrated embodiment, footboard user interface 62 includes a substantially complete set of controls for controlling patient support apparatus 20, while user interfaces 58 and 60 include a selected subset of those controls. In addition, one or more user interfaces may be communicatively coupled to patient support apparatus 20 but physically positioned remote from patient support apparatus 20, such as, but not limited to, a computer tablet, a smart phone, a computer station, etc.

The mechanical construction of patient support apparatus 20 may be the same as, or nearly the same as, the mechanical construction of the Model 3002 S3 bed manufactured and sold by Stryker Corporation of Kalamazoo, Mich. This mechanical construction is described in detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that patient support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. No. 8,689,376 issued to Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are hereby incorporated herein by reference. The mechanical construction of patient support apparatus 20 may also take on forms different from what is disclosed in the aforementioned references.

Figure 4:
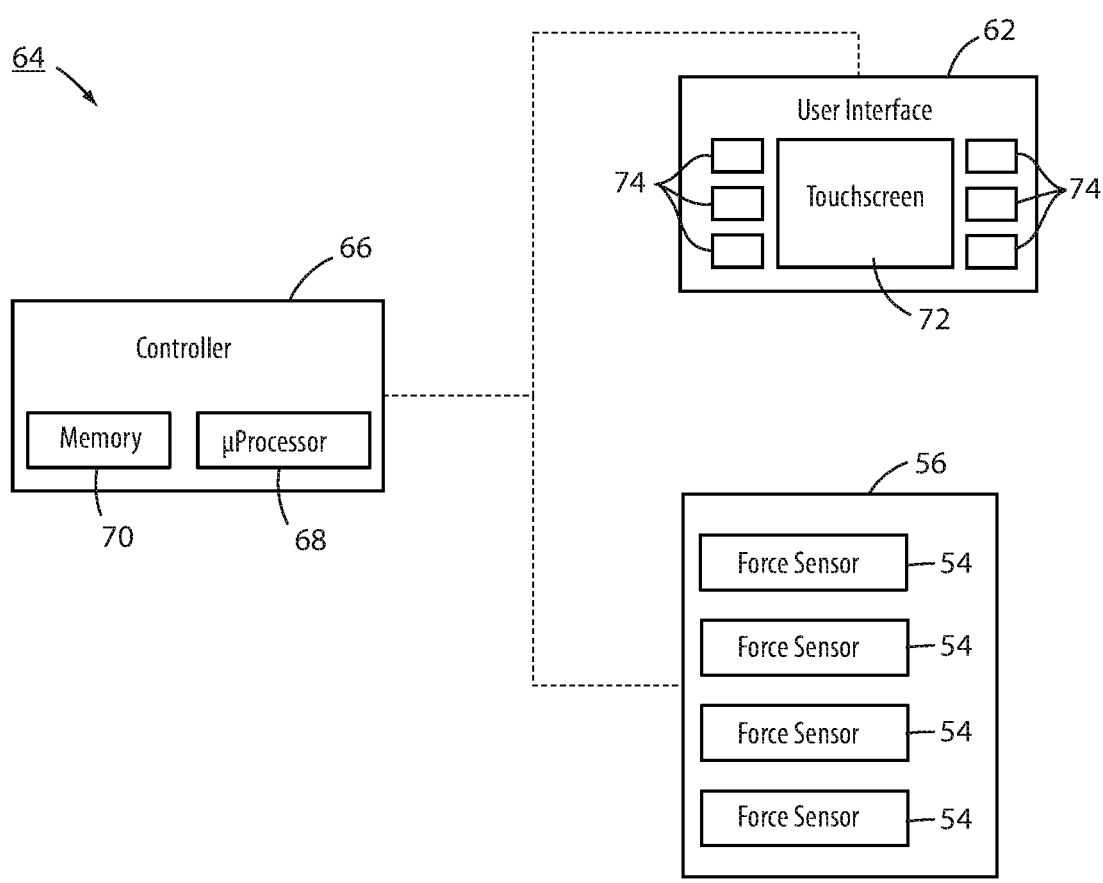
FIG. 4 is a diagram of a control system of the patient support apparatus of FIG. 1.

Referring additionally to FIG. 4, the patient support apparatus 20 includes a control system 64 provided to control operation of various components of the patient support apparatus 20. The control system 64 includes a controller 66 having one or more microprocessors 68 for processing instructions or for processing an algorithm stored in a memory 70 accessible to microprocessor 68 to control operation of the various components.

Controller 66 is constructed of any electrical component, or group of electrical components, that are capable of carrying out the functions described herein. In many embodiments, controller 66 is a conventional microcontroller, although not all such embodiments need include a microcontroller. In general, controller 66 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 66 in carrying out the functions described herein, as well as the data necessary for carrying out these functions, are stored in memory 70.

Controller 66 is in communication with footboard user interface 62, as shown in FIG. 4. Controller 66 also communicates with the user interfaces 58 and 60 that are positioned on patient support apparatus 20, although these are not shown in FIG. 4 for purposes of clarity. Footboard user interface 62 includes a display 72 and a plurality of controls 74. Display 72 is a touchscreen in at least some embodiments, although it will be understood that a non-touchscreen display may alternatively be used. The touchscreen 72 can be a multi-touch screen display capable of recognizing more than one point of contact. Controls 74 are shown in FIG. 4 as touch sensitive controls that may be physically implemented in a variety of different manners. In some embodiments, controls 74 are implemented as capacitive sensors positioned adjacent touchscreen 72 that capacitively detect when a user presses them. In other embodiments, controls 74 are implemented as buttons, switches, or other types of force or touch-sensitive device. In still other embodiments, one or more of the functions controlled by controls 74 may be incorporated into corresponding icons and/or visual controls displayed on touchscreen 72. Still other variations are possible.

With respect to the scale/exit detection system 56, user interface 62 communicates with controller 66 and enables a user of patient support apparatus 20 to control one or more aspects of the scale/exit detection system 56. The controls 74 allows a user to control various aspects of the scale/exit detection system 56, such as, but not limited to, taking a patient's weight and logging equipment or other non-patient weight added to or removed from the support deck 30. The display 72 displays information regarding scale/exit detection system 56.

Figure 5:
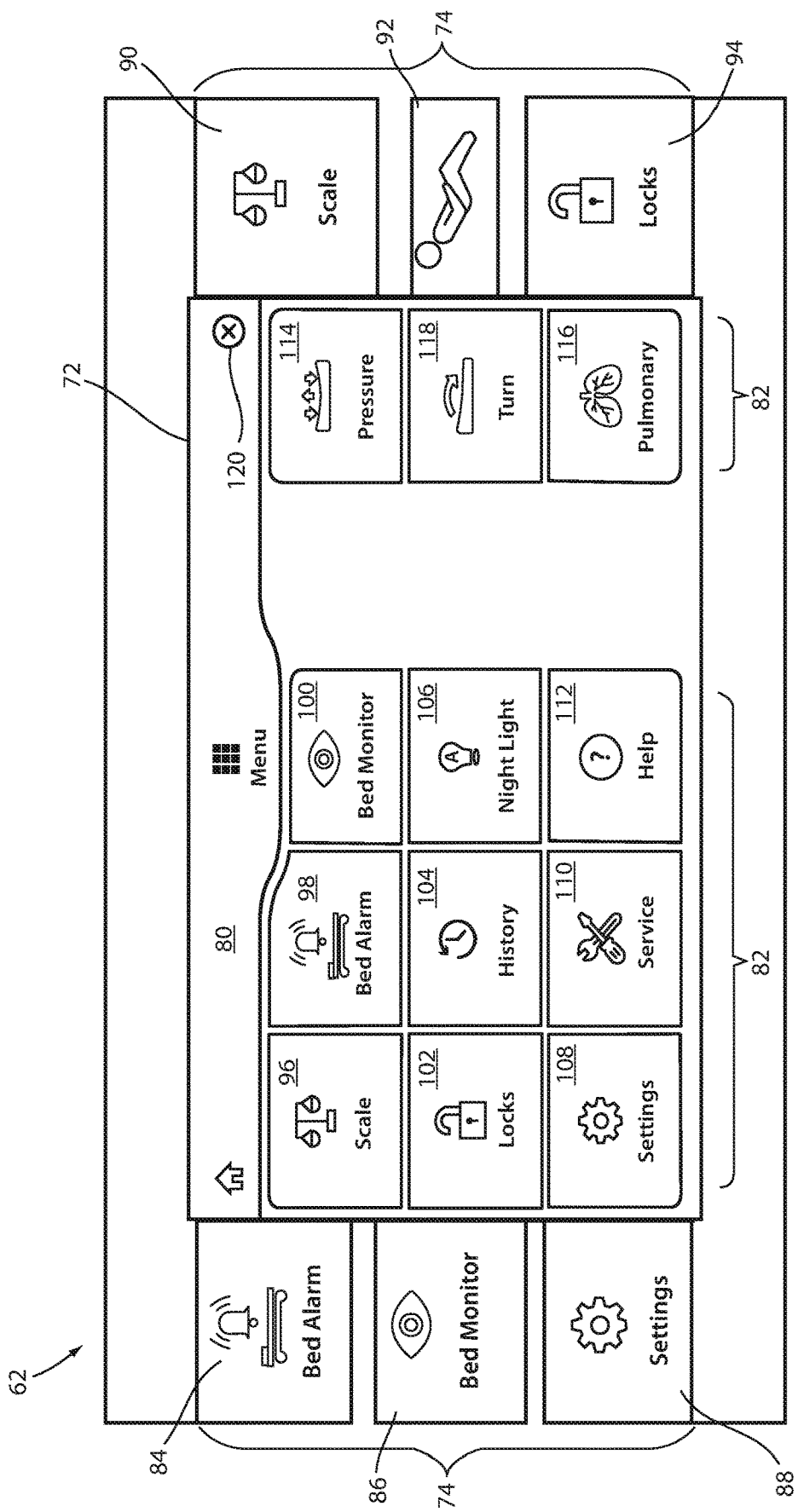
FIG. 5 is a diagram of a user interface of the patient support apparatuses of FIG. 1, the user interface having a touchscreen.

FIG. 5 illustrates in more detail one manner in which user interface 62 (or another user interface 58 or 60 on patient support apparatus 20) is implemented. User interface 62 includes a menu screen 80 displayed on the touchscreen 72 having a plurality of touchscreen controls 82, and a plurality of non-touchscreen controls 74 that are positioned adjacent to touchscreen 72.

In the particular example of FIG. 5, the non-touchscreen controls 82 include a bed alarm control 84, a bed monitor control 86, a settings control 88, a scale control 90, a position control 92, and a locks control 94, although it will be understood that in different embodiments, any of these controls could be implemented as a touchscreen control 82. Each of these controls, when activated, causes controller 66 to displaying a corresponding control screen on touchscreen display 72. For example, when the scale control 90 is pressed, controller 86 displays a scale screen (e.g. scale home screen 122 of FIG. 7) on touchscreen 72. The scale screen is used by a caregiver or other user to take a weight reading of an occupant of the patient support apparatus 20 using the scale/exit detection system 56, as well as to control other aspects of the scale system, as described in further detail below.

Examples of control screens for controls 84, 86, 88, 92, and 94 are not provided herein as they are not necessary for understanding the inventive concepts disclosed herein. Briefly, when bed alarm control 84 is activated, controller 66 displays an exit detection control screen (not shown) that enables the user to arm and/disarm the exit detection function of the scale/exit detection system 56, as well as to change one or more of the settings associated with the exit detection function. Activating the bed monitor control 86 brings up a bed monitor control screen (not shown) on touchscreen 72 that includes controls for controlling a bed monitoring system of the patient support apparatus 20, including controls for activating and deactivating the bed monitoring system and changing one or more settings of the bed monitoring system. Settings control 88, when activated, causes a settings screen (not shown) to be displayed that enables a user to change one or more settings of the patient support apparatus 20. Position control 92, when activated by a user, causes controller 66 to display a position control screen (not shown) that includes a plurality of controls enabling the user to change a configuration or position of the patient support apparatus 20, such as changing the height or angle of the litter frame 16 or the configuration of the support deck 18. Locks control 94, when activated by a user, brings up a lock control screen (not shown) is used to prevent the configuration or position of the patient support apparatus 20 from being changed at one of the other user interfaces 58 or 60.

The touchscreen controls 82 may perform a variety of different functions, and the number, function, lay-out, size, and/or other characteristics of these controls may vary from what is shown in FIG. 5, and may also vary depending upon what screen is being displayed at a given time by touchscreen 72.

Some non-limiting examples of screens and touchscreen controls are provided in FIGS. 5 and 7-20. FIG. 5 illustrates the menu screen 80 displayed on the touchscreen 72. Other screens that are displayable on touchscreen 72 are used to control the scale/exit detection system 56 of the patient support apparatus 20, examples of which are shown in FIGS. 7-20.

Menu screen 80 may be displayed initially after the patient support apparatus 20 is powered on, or it may be displayed in response to a user navigating to it from another screen. It will be understood that the particular layout shown in FIG. 5 is only one of a large variety of different ways in which controller 66 may present a menu screen.

As can be seen in FIG. 5, menu screen 80 includes a plurality of touchscreen controls, including at least a scale control 96. User-selection of the scale control 96 displays a different screen, particular to the scale/exist detection system 56, on the touchscreen 72, examples of which are given below. Additional touchscreen controls include a bed alarm control 98, a bed monitor control 100, a lockout control 102, a history control 104, a night light control 106, a settings control 108, a service control 110, a help control 112, a pressure control 114, a lateral rotation control 116 and a turn assist control 118. User-selection of any one of these controls 98-118 displays a different screen, particular to the associated control, on the touchscreen 72. Examples of screens for controls 98-118 are not provided herein as they are not necessary for understanding the inventive concepts disclosed herein. Briefly, the bed alarm control 98, bed monitor control 100, lockout control 102, and settings control 108 are touchscreen duplicates of the non-touchscreen controls 84, 86, 88, and 94, respectively. The history control 104 displays a history screen (not shown) which includes historical information on the operation or maintenance of the patient support apparatus 20. The night light control 106 displays a night light screen (not shown) which includes control inputs for a night light of the patient support apparatus 20. The service control 110 displays a service screen (not shown) which includes information on service topics such as how to perform or request maintenance on the patient support apparatus 20. The help control 112 displays a help screen (not shown) which includes information on help topics such as the use, operation, and functions of the patient support apparatus 20. The lateral rotation control 116 displays lateral rotation control screen (not shown) which includes control inputs for controlling a lateral rotation therapy function of the mattress to rotate a patient supported on the mattress side to side in an effort to reduce pulmonary complications of immobility. The turn assist control 118 displays turn assist control screen (not shown) which includes control inputs for controlling a turn assist therapy function of the mattress to turn or rotate a patient supported on the mattress laterally to one side for a period of time to help reposition the patient, such as to prevent bed sores. The pressure control 114 displays a pressure redistribution therapy control screen (not shown) which includes control inputs for operating a mattress in a pressure redistribution mode. A cancel control 120 allows the user to return to a home screen or the previously displayed screen.

Figure 6:
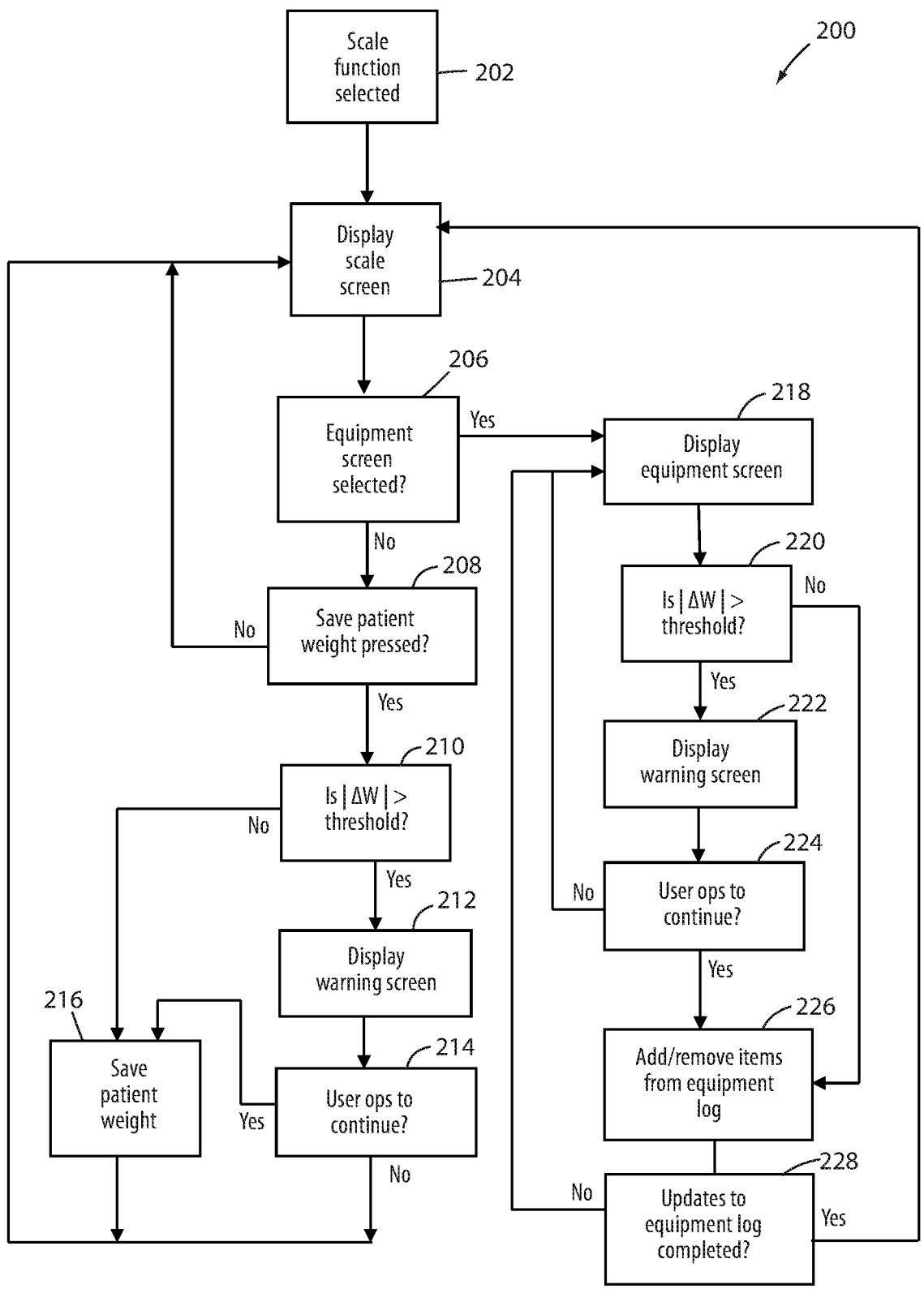
FIG. 6 is a weight management algorithm executed by the controller of the control system according to one embodiment.
Figure 7:
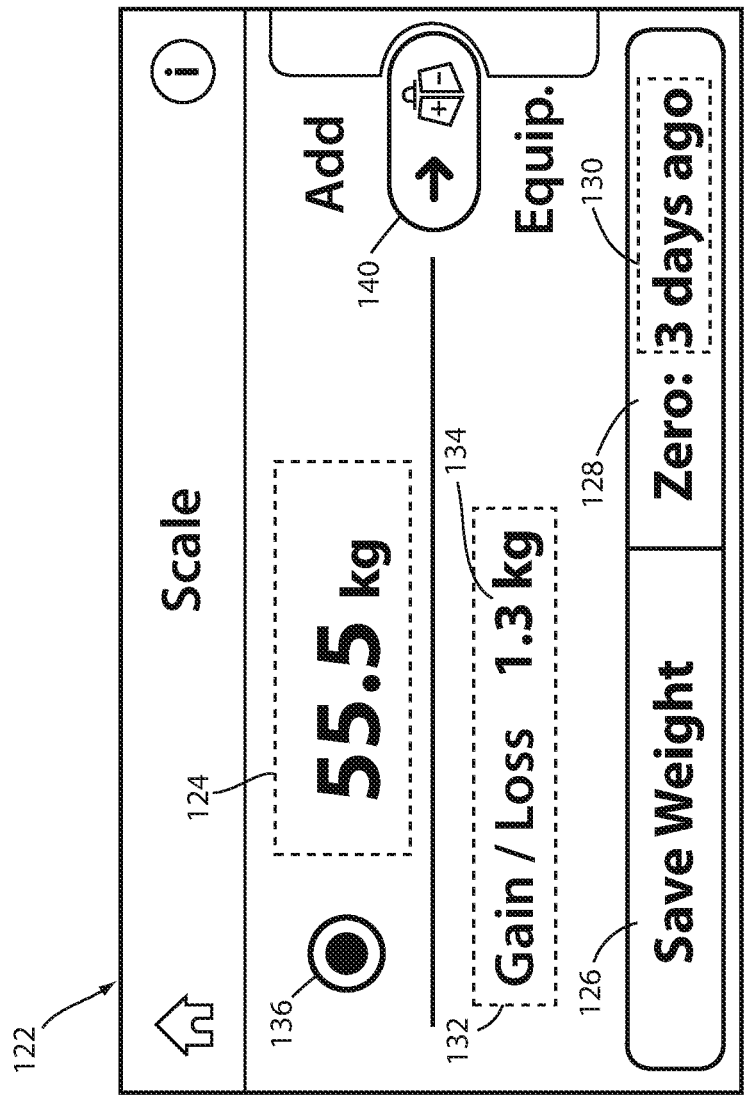
FIG. 7 is an illustrative scale screen that may be displayed on the touchscreen of FIG. 5, such as, but not limited to, in response to a user pressing the scale control of FIG. 5.

When either scale control 90 or 96 on the user interface 62 of FIG. 5 is selected, controller 66 displays scale home screen 122, an example of which is shown in FIG. 7, on touchscreen 72. From scale home screen 122, the user is able to take a patient's weight reading, review changes in the patient's weight, update the equipment weight log by either adding or removing items from the log, and perform other functions associated with the scale. When controller 66 displays scale home screen 122, it begins following a weight management algorithm 200, one example of which is shown in FIG. 6.

Weight management algorithm 200 begins at step 202 when the scale function is selected by the user. The scale function is selected when the user activates either the dedicated scale control 90 of FIG. 5 or the touch screen scale control 96 of FIG. 5. After the scale function is selected, controller 66 proceeds to step 204 where it displays the scale home screen 122, one example of which is shown in FIG. 7. Although there are other functions that controller 66 is enabled to carry out from scale home screen 122, algorithm 200 is described herein as including only two functions: weighing the patient and updating the equipment weight log. It will be understood that this is done merely for conciseness and that controller 66 is configured to carry out additional weight-related functions from scale home screen 122, such as, but not limited to, zeroing the scale, reviewing weight histories, etc.

While the scale home screen 122 is being displayed, controller 66 monitors the touchscreen to see if the user has activated one or more functions associated with screen 122. If the user presses on an equipment icon 140, controller 66 moves to step 218 where it begins a process to be described below that allows a user to update the contents of an equipment log. If the user does not press on the equipment icon 140, controller 66 moves to step 208 where it allows the user to perform other weight related functions, such as saving the patient's current weight to a memory on the patient support apparatus 20.

Turning first to step 208, controller 66 monitors whether the user presses the save weight control 126 or not (and, as noted, also monitors other user-actions and reacts accordingly, although these actions are not shown in FIG. 6 and not described in algorithm 200). The save weight control 126, as will be described in greater detail below, is used to save a new weight reading for a patient positioned on litter frame 28. If the user does not press the save weight control 126, controller 66 returns to step 204 and continues to display the scale home screen 122. If the user presses the save weight control 126, controller 66 moves to step 210.

At step 210 (FIG. 6), controller 66 calculates the current total weight reading (gross weight minus the tare weight and any equipment weight that is stored in the equipment log). Controller 66 then compares this value to the last saved patient weight. The difference is identified in FIG. 6 as ΔW and corresponds to an initial estimate of the patient's weight change since his or her weight was last recorded. However, as will be explained in greater detail below, this estimate may be incorrect because some of the weight change may have been due to added or removed equipment that wasn't entered into the equipment log. Thus, controller 66 displays additional screens and/or information in order to allow the user to confirm whether this assumption is true or not, as will be described below.

At step 210, controller 66 compares the absolute value of the ΔW value to a threshold. If the absolute value of ΔW is greater than the threshold, controller 66 moves to step 212. If the absolute value of ΔW is less than or equal to the threshold, controller 66 moves to step 216. Turning first to step 212, controller displays a warning screen, such as, but not limited to, one of the warning screens of FIG. 12 or 13, when the absolute value of ΔW is greater than the threshold. The warning screen is displayed because the amount of change in the patient's weight since he or she was last weighed (and saved) exceeds what controller 66 deems to be typical (as determined by the comparison to the threshold at step 210). Thus, there exists the possibility that the change in the patient's weight is at least partially due to equipment having been added to, or removed from, litter frame 28 since the last time the patient's weight was saved. The warning screen displayed at step 212 therefore notifies the user that he or she may wish to visually double check what items are or are not on the litter frame before saving the patient's weight in order to confirm that the saved patient's weight reading will be accurate.

Figure 12:
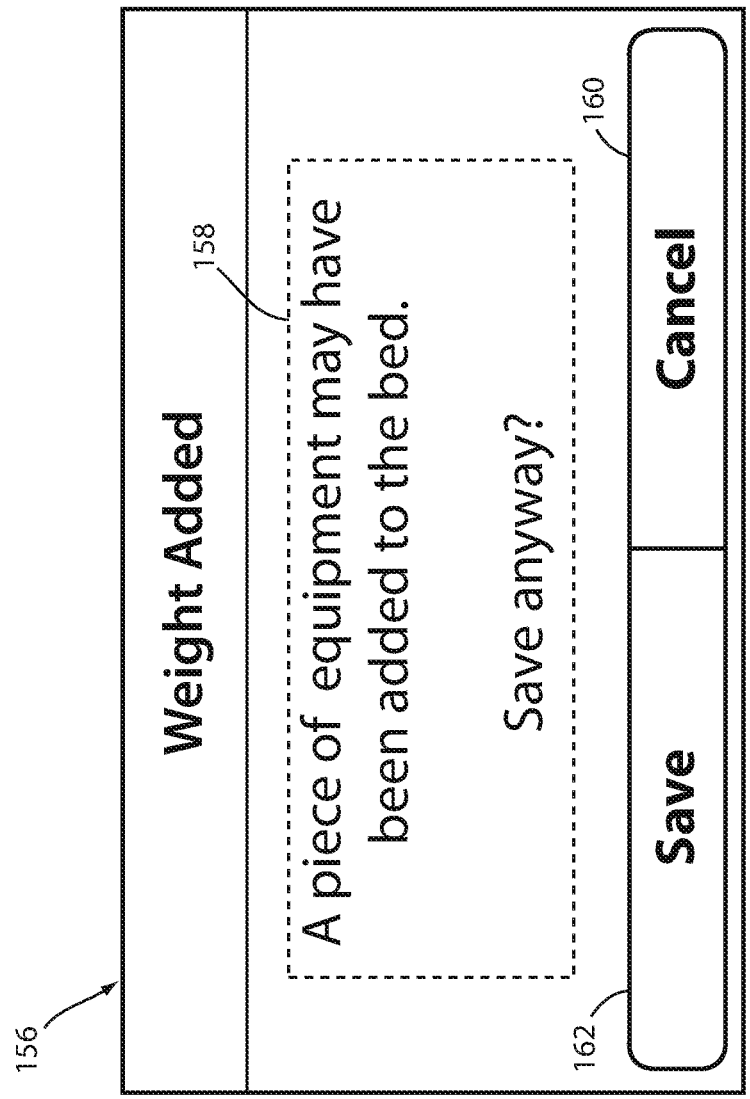
FIG. 12 is a first illustrative warning screen that is displayed prior to a user saving a patient weight reading when the current weight reading has increased from the prior patient weight reading by more than a threshold.
Figure 13:
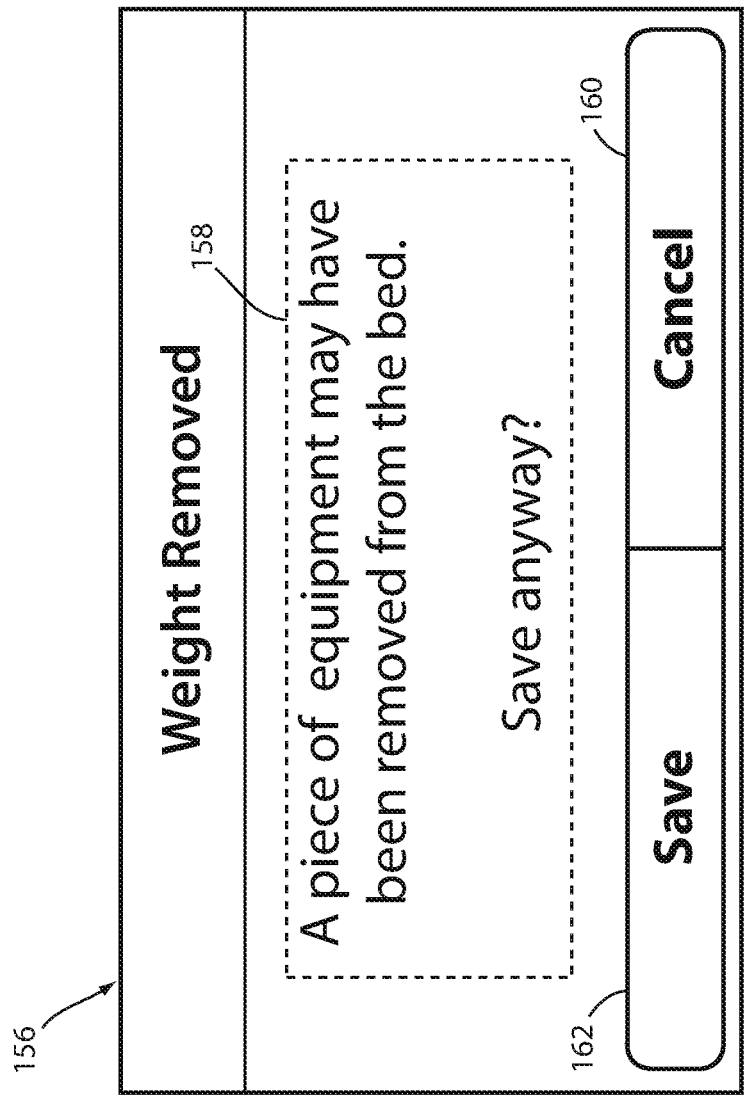
FIG. 13 is a second illustrative warning screen that is displayed prior to a user saving a patient weight reading when the current weight reading has decreased from the prior patient weight reading by more than the threshold.

The warning screens do not prevent the user from saving the patient's weight when the ΔW value exceeds the threshold, but simply provide a cautionary reminder to the user to visually inspect the litter frame 28 before saving the patient's weight. The user can therefore proceed to save the weight by simply pressing on a save weight control on the warning screen. One example of such a save weight control 160 is shown in FIGS. 12 and 13. By pressing on this control, the current patient weight reading (which is equal to the current gross weight minus the tare weight minus the weight of any items currently in the equipment log) is saved to the memory of patient support apparatus 20. This newly saved patient weight is marked in memory as the most recently saved weight and then becomes the weight used when determining ΔW the next time algorithm 200 executes step 210 (or step 220, described further below).

The pressing of one of the save weight controls 160 of FIG. 12 or 13 is represented in FIG. 6 by the user opting to continue in step 214. That is, after displaying the warning screen at step 212, the user can simply save the currently measured weight as the patient's current weight by opting to ignore the warning message. This decision is represented by the user opting "yes" in step 214, which causes controller 66 to proceed to step 216, where it saves the patient's weight. From step 216, controller 66 proceeds back to displaying the scale home screen 122 at step 204.

If the user opts not to save the currently measured weight as a new patient weight reading at step 214, controller 66 returns to displaying the scale screen at step 204, as indicated in FIG. 6. In many instances, the user may elect not to save the currently measured patient weight at that time because he or she wants to add an item of equipment to, or remove an item of equipment from, the equipment weight log, and this procedure can be performed by starting at the scale home screen 122 displayed at step 204. More specifically, the procedure of updating the equipment weight log is performed by selecting the equipment icon 140 from the scale home screen of FIG. 7. This corresponds to selecting the equipment screen in step 206 of algorithm 200, at which point controller 66 proceeds to step 218 of algorithm 200.

Figure 14:
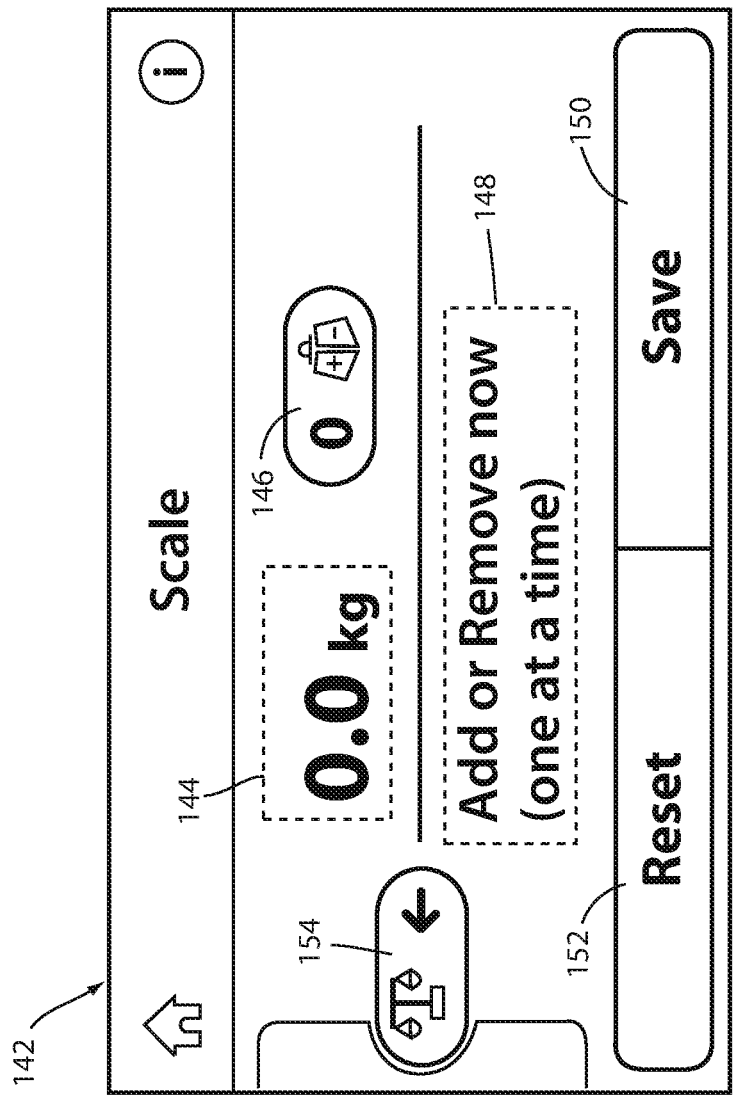
FIG. 14 is an illustrative equipment screen that is displayed on the touchscreen of FIG. 5 when a user wishes to add weight to, or remove weight from, an equipment weight log maintained by the patient support apparatus.

At step 218 of algorithm 200, controller 66 display an equipment log screen that allows a user to make changes to the equipment log. One example of an equipment log screen is shown the equipment log screen 142 shown in FIG. 14. Once this screen is displayed, the user updates the equipment log by either adding equipment to the litter frame 28 one item at a time, or by removing equipment from the litter frame one item at a time. For each item that is added or removed, the user presses a save control (e.g. save control 150 of FIG. 14) that saves the addition of the item to, or the removal of the item from, the equipment weight log. Thus, once the user brings up screen 142, the user is prompted to add or remove the first item, press the save control 150 after it has been added or removed, and then repeat those steps for any additional items until the user is done updating the equipment log. When the user is done (or at any other time), he or she can return to the scale home screen 122 by pressing on the scale icon 154 (FIG. 14). This is represented by step 228 in algorithm 200.

In order to ensure that all equipment is properly added to and removed from the equipment weight log, algorithm 200 includes a threshold weight checking step 220 that is similar to the threshold step 210. Indeed, in some embodiments, the value of the threshold used at step 220 is the same as the value used at step 210, although it will be recognized that it is not necessary to use the same value for both threshold checking steps 210 and 220. At the threshold weight checking step 220, controller 66 compares the ΔW value—which is the same ΔW used and discussed above with respect to step 220—to the threshold. If the ΔW value is greater than the threshold, controller 66 proceeds to step 222 and displays a warning screen, such as, but not limited to, one of the warning screens shown in FIG. 18 or 19. If the ΔW value is less than or equal to the threshold, controller 66 proceeds to step 226 where it prompts the user to add or remove one item at a time to litter frame 28.

Figure 18:
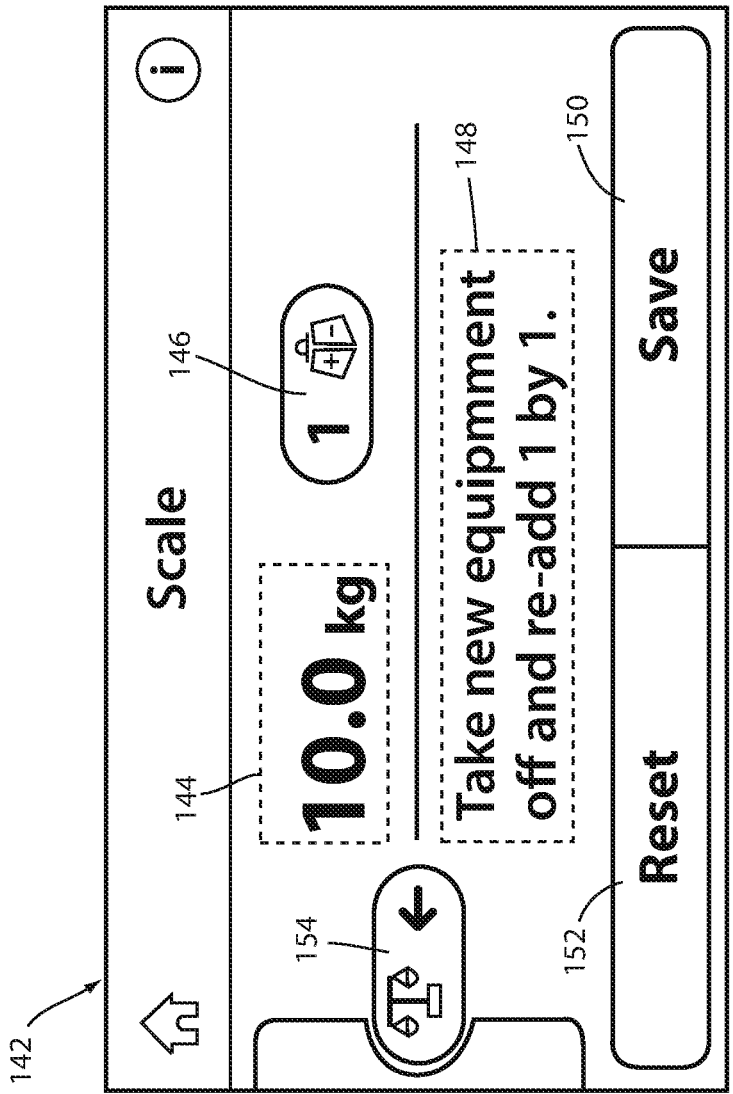
FIG. 18 is a third illustrative warning screen that is displayed when a piece of equipment may have been added too soon for proper entry into the equipment weight log of the patient support apparatus.
Figure 19:
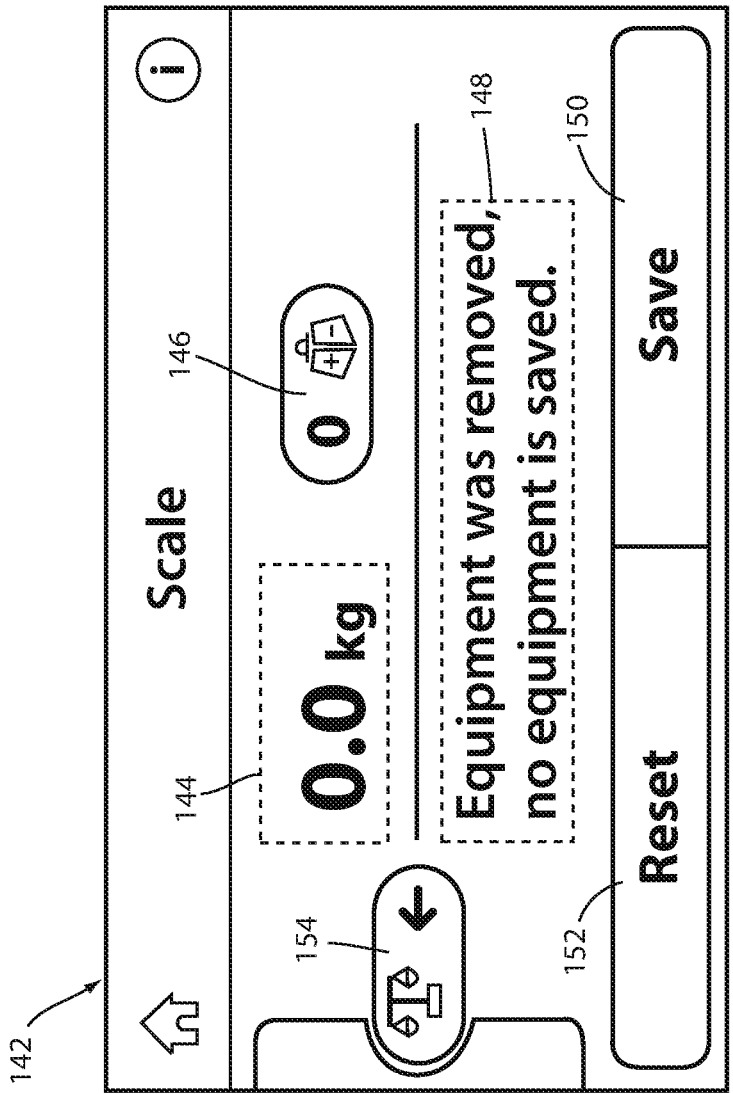
FIG. 19 is a fourth illustrative warning screen that is displayed when a piece of equipment may have been removed too soon for proper removal from the equipment weight log of the patient support apparatus.

When controller 66 proceeds to step 222, it displays a warning screen because there is the potential that the user has either added a piece of equipment to the litter frame, or removed a piece of equipment from the litter frame 28, prior to bringing up equipment log screen 142. That is, there is a potential that the user has added or removed equipment from the litter frame 28 prior to controller 66 being instructed that such weight changes are to be entered into the equipment weight log. In many instances, this can happen when a user enters the room in which patient support apparatus 20 is positioned while carrying a piece of equipment and then sets the equipment down on the litter frame before proceeding to access touchscreen 72. In such instances, the equipment has been added to the litter frame 28 before the user has brought up equipment log screen 142 and controller 66 has not been instructed to detect the weight of the equipment. A warning screen, such as shown in FIG. 18 or 19, therefore tells the user that a significant weight change (i.e. greater than the threshold) has occurred since the patient's weight was last saved, and that if the weight change is due to equipment being added or removed, the user needs to either manually remove the prematurely-added equipment from litter frame 28 and re-add it, or to manually replace the prematurely removed equipment on litter frame 28 and then remove it. This manual re-addition or re-removal process allows controller 66 to monitor the precise weight change that occurs during this re-addition or re-removal process, and thereby determine the correct weight to either add to the equipment log or remove from the equipment log.

As with the patient weight saving process of algorithm 200 (e.g. steps 208-216), the equipment log updating process (e.g. steps 218-228) includes the ability of the user to ignore the warning screen. Thus, when controller 66 detects a weight change (ΔW) greater than the threshold and displays the warning screen at step 222, the user can opt to ignore the weight change and continue with the updates to the equipment log. This is done by pressing a "continue" control, or the like (not shown), on the warning screen that brings the user to step 226. By pressing this continue control, the user is effectively instructing controller 66 that the weight change ΔW is actually a weight change of the patient, and not a weight change due to any pieces of equipment (or other non-patient items) being added or removed. At step 226, the user adds one piece of equipment at a time to the litter frame and saves them into the equipment log, or removes one piece of equipment at a time from the litter frame 28 and removes them from the equipment log. When the user is done at step 228, he or she is brought back to the scale home screen 122, which is re-displayed at step 204 (and updated to reflect any changes that were made to the equipment log).

During the equipment log updating process, controller 66 repetitively monitors changes in weight applied to litter frame 28. Such changes are detected by force sensors 54. When a user is at the add/remove step 226 of algorithm 200, controller 66 monitors and records the weight readings multiple times a second. When the user adds a piece of equipment during step 226, controller 66 detects this change in weight and compares it to the previous weight (or an average of the previous weight readings taken during step 226 in the moments before the user has added the equipment). Controller 66 then computes the difference between these two weights, which corresponds to the weight of the added item, and updates the equipment log by adding this weight (and one more piece of equipment) to the equipment log. If the user removes a piece of equipment during step 226, controller 66 does essentially the reverse process. That is, controller 66 monitors the weight readings at step 226 in the moments before the piece of equipment is removed (and records them, or an average of them), records the weight readings after the piece of equipment is removed, determines the difference (which equals the weight of the item removed), and then subtracts this amount of weight from the equipment log (as well as decrementing the total number of items in the log by one). These add or remove processes are repeated for any many pieces of equipment the user wishes to add or remove from the equipment log.

During the execution of algorithm 200, controller 66 displays a number of different screens and information on touchscreen 72. Examples of these screens and information are discussed below with respect to FIGS. 7-20. It will be understood that these specific screens and information are merely examples of the type of information that controller 66 may displays, and that these examples are provided herein to provide further explanation of the features of algorithm 200. Other types of screens and/or information may be displayed during the execution of algorithm 200. Further, it will also be understood that algorithm 200 may be modified in a variety of different manners, some of which are discussed in greater detail below.

FIG. 7 illustrates the scale home screen 122, which is displayed after the scale control 90 or 96 of FIG. 5 is pressed. The display of screen 122 corresponds to step 204 of algorithm 200. The display of scale home screen 122 includes an indicator 124 of the patient's weight, as determined by the scale/exit detection system 56, i.e. the force sensors 54, and a save weight control 126 used to store the patient's weight reading.

The scale home screen 122 also includes a zero control 128 that is used to calibrate the scale system 56 by establishing a tare weight that is deducted from the gross weight detected by the force sensors 54. The gross weight includes the weight of the patient and of the litter frame 28 and/or other components of the patient support apparatus 20 that the force sensors 54 support. The zero control 128 is often used before placing a new patient on the patient support apparatus 20.

Upon user-selection of the zero control 128, the controller 66 is operable to save the load registered by the scale/exit detection system 56, i.e. the force sensors 54, as a tare weight. Also upon user-selection of the zero control 128, the controller 66 is operable to delete previous patient weight data. The zero control 128 therefore acts as a quick, one-touch new patient setup, and clears previous weight data.

The zero control 128 is used with no patient in the patient support apparatus 20 to ensure an accurate tare weight is deducted from subsequent gross weight readings. By taking a weight reading without a patient on the patient support apparatus 20, the weight of the litter frame 28 and/or other non-patient components of the patient support apparatus 20 that the force sensors 54 support is established as a tare weight. Deduction of the tare weight from subsequent gross weight readings provides a patient-assumed weight, which is displayed numerically by the patient weight indicator 124 on screen 122. The patient-assumed weight is only an assumed weight because it is still possible for non-patient items, such as, but not limited to, equipment to be added to or removed from the litter frame 28 after the tare weight has been established and/or after the patient is positioned on litter frame 28. In order to account for the weight of these non-patient items, patient support apparatus 20 is equipped with the equipment log mentioned above. The equipment log maintains a record of the number of non-patient items that have been added to litter frame 28 after the tare weight was established, as well as their total weight. The total weight of the items in the equipment log is used to provide a correct indication of the patient's weight. That is, from the gross weight reading measured by the force sensors 54, controller 66 subtracts both the tare weight and the total weight of the items stored within the equipment log. The result is the patient's weight.

If a patient is in the patient support apparatus 20 when the zero control 128 (FIG. 7) is selected, or if the scale system 56 otherwise detects a weight above a predetermined maximum weight for the tare function, a warning or error message is displayed on the user interface informing the user that the patient support apparatus 20 should not be zeroed with a patient on the apparatus 20.

The zero control 128 can include an indication 130 of when the system was last calibrated, i.e. when a tare weight was last saved. In the example of the screen 122 shown in FIG. 7, the indication 130 includes text showing that a tare weight was saved 3 days ago.

The scale home screen 122 also includes a gain/loss indicator 132 comprising a numeric value 134 representative of the change between the patient's current weight and a previously saved weight of the patient. To determine if the patient's weight has changed, the controller 66 compares the current patient weight, as determined by input from the force sensors 54, to the last saved weight for the patient. The controller 66 then displays the value of the patient' weight change on the screen 122 as the numeric value 134. In the example of the screen 122 shown in FIG. 7, the gain/loss indicator 132 shows that the patient's weight has increased by 1.3 kg.

The scale home screen 122 also includes a gain/loss information icon 136 comprising an indication of whether the patient's weight has increased, decreased, or has not changed since last weighing the patient. To determine if the patient's weight has changed, the controller 66 compares the current patient weight, as determined by input from the force sensors 54, to the last saved weight for the patient. If the patient's weight has increased, the information icon 136 displays an up arrow. If the patient's weight has decreased, the information icon 136 displays a down arrow. If the patient's weight has not changed, information icon 136 displays no arrow, as shown in FIG. 7.

Figure 8:
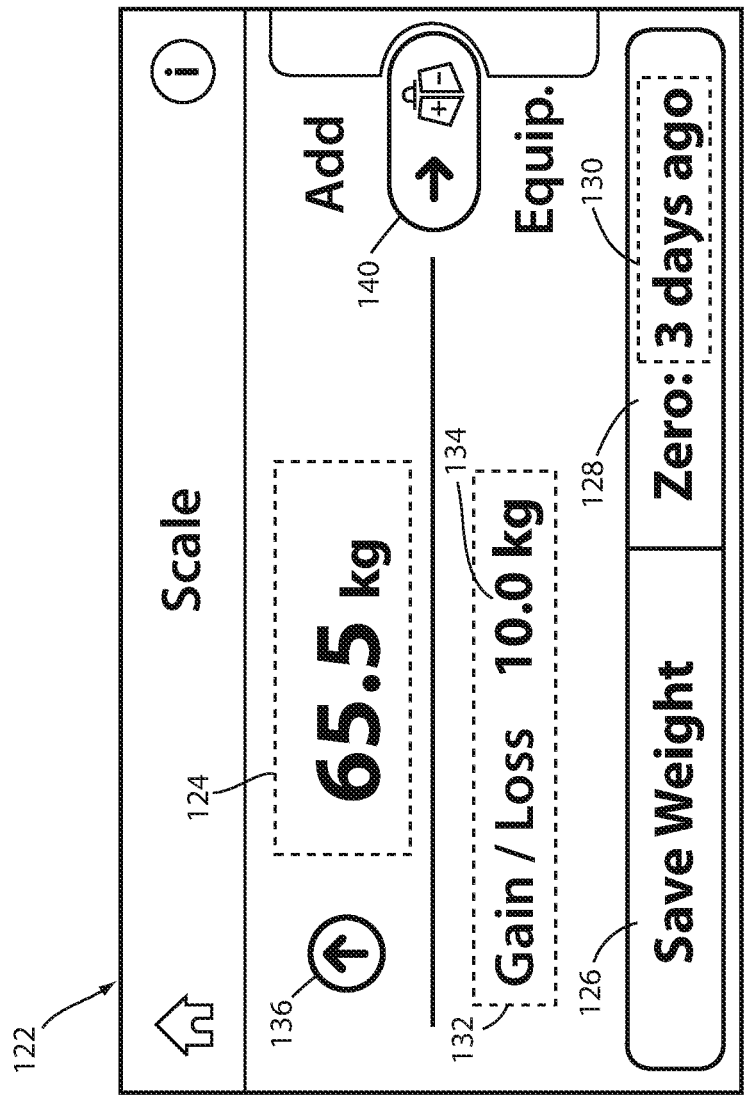
FIG. 8 is the scale screen of FIG. 7 modified to show that a patient's weight has increased since the patient's weight was previously saved.
Figure 9:
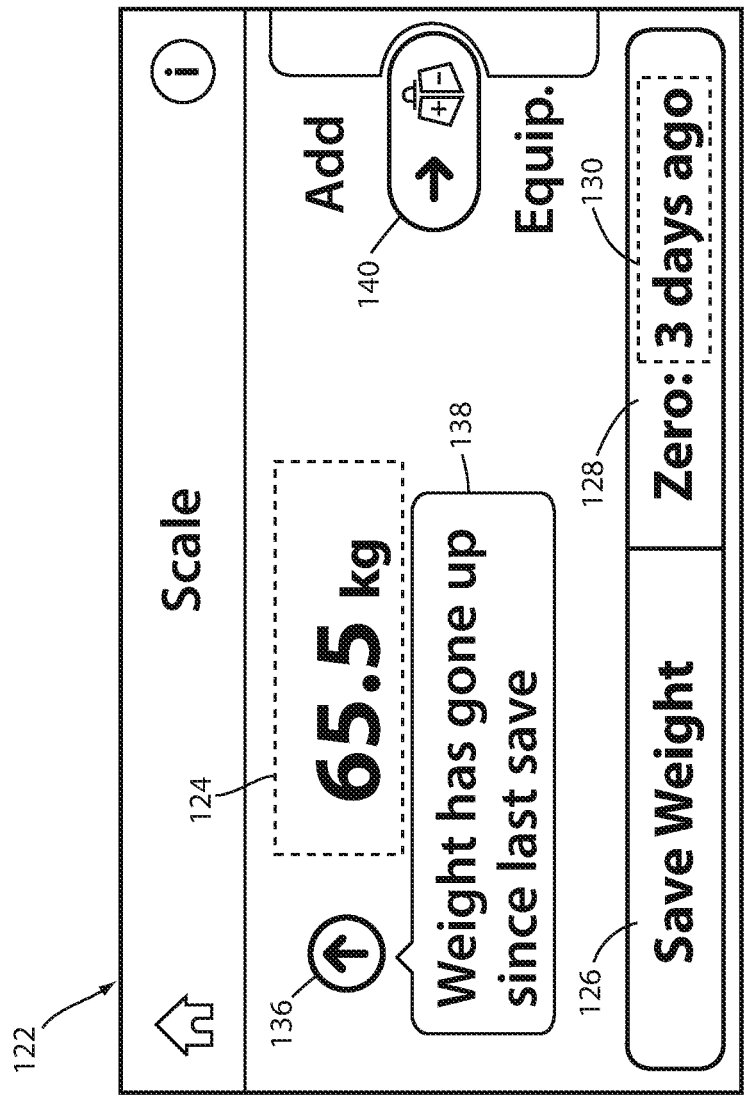
FIG. 9 is the scale screen of FIG. 8 further modified with additional information regarding the patient's increase in weight.

FIG. 8 shows the scale home screen 122 in a case where a patient's weight has increased since the previously waved patient weight. As can be seen therein, information icon 136 includes an up arrow. In some embodiments, the up arrow is displayed in a color different from the other displayed content, or a color different from the rest of information icon 136 (e.g. the circle surrounding the arrow) so that the presence of the arrow is more easily noticed, thereby more easily catching the eye of the user. In the example of FIG. 8, scale home screen 122 also shows that no equipment has been logged into the equipment log, as shown by the equipment icon 140. In the illustrated example, the gain/loss indicator 132 shows a weight gain of 10.0 kg. Upon user-selection of the information icon 136, the controller 66 is configured to display text 138, an example of which is shown in FIG. 9. Text 138 provides further information about the weight gain, such as a textual explanation that the load supported by the litter frame 28 has increased since last weighing the patient.

Figure 10:
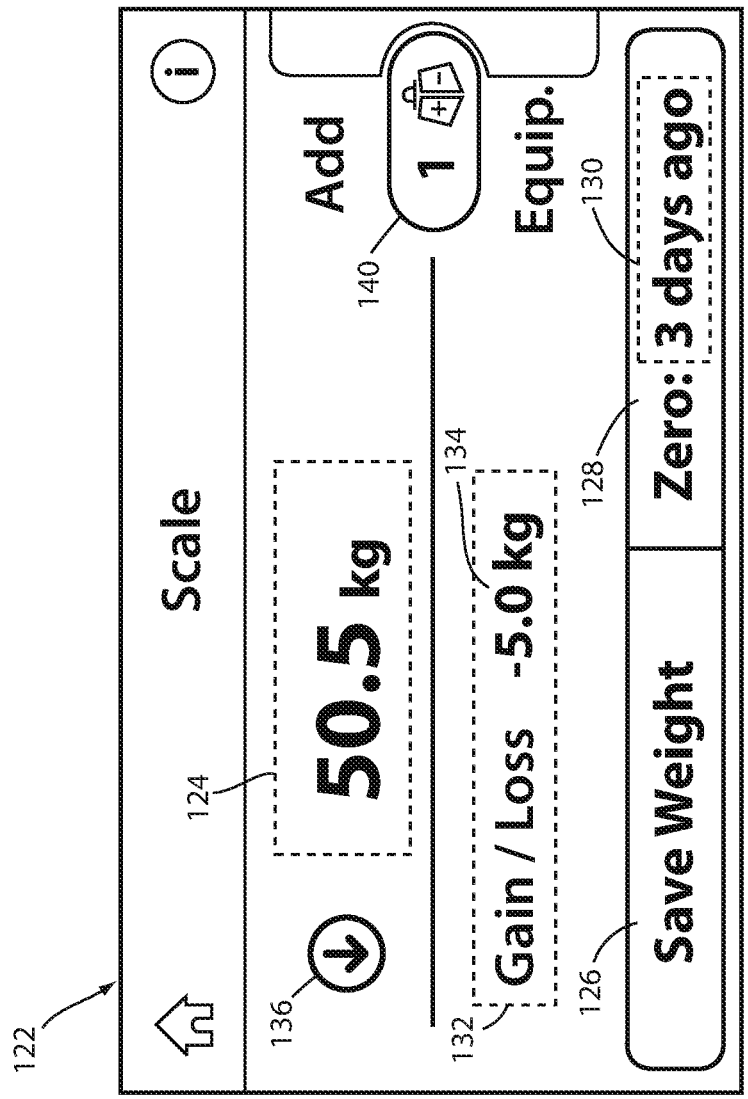
FIG. 10 is the scale screen of FIG. 7 modified to show that a patient's weight has decreased since the patient's weight was previously saved.
Figure 11:
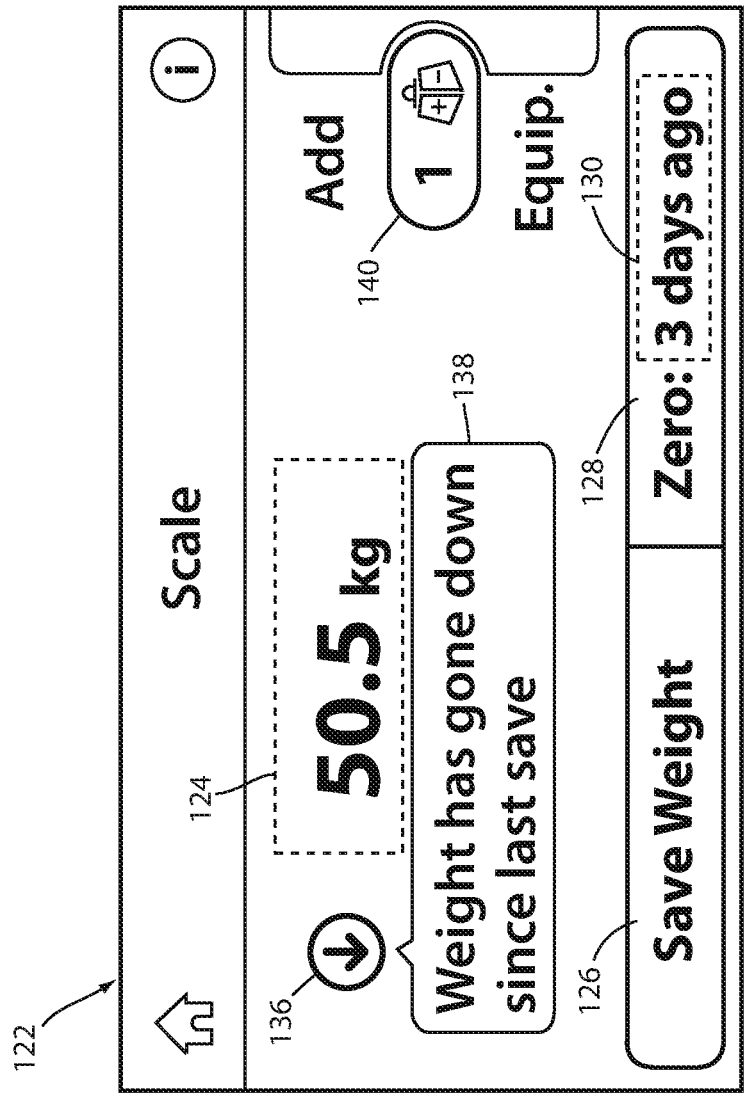
FIG. 11 is the scale screen of FIG. 10 further modified with additional information regarding the patient's decrease in weight.

FIG. 10 shows the scale home screen 122 in a case where a patient's weight has decreased since the previous time the patient's weight was saved. This decrease in weight is indicated by the down arrow added to information icon 136. As with the case of the up arrow of FIG. 8, the down arrow of FIG. 10 may be displayed in a color that contrasts from its immediate surroundings in order to stand out and catch the eye of the user. FIG. 10 also shows that one piece of equipment weighing 5.0 kg has previously been logged into the equipment log, as indicated by the equipment icon 140. In the illustrated example, the gain/loss indicator 132 shows a weight loss of 5.0 kg. Upon user-selection of the information icon 136, the controller 66 is configured to display text 138, as shown in FIG. 11, explaining that the load supported by the support deck 30 has decreased since last weighing the patient.

Upon selection of the save weight control 126 of the scale home screen 122 (any of FIGS. 7-11), controller 66 follows steps 208 through 216 of algorithm 200. That is, controller 66 determines whether the weight change threshold has been exceeded at step 210. In one example, the threshold value can be 2.0 kg. In another example, the threshold value can be 5 lbs. (approximately 2.27 kg). In still other examples, other values may be used. Regardless of the specific value, controller 66 compares at step 210 the currently measured weight (which is equal to the gross weight minus the tare weight minus the weight of any equipment that has been stored in the equipment log) with the last weight reading of the patient that was saved. If that difference exceeds the threshold, then controller 66 alerts the user at step 212 that the weight change may be due to equipment either being added or removed. In such a case, controller 66 prompts the user to consider whether the weight change is due to an actual change in the patient's weight, or possibly due to equipment being added or removed. The user is free to ignore the prompt and continue to save the weight, but the prompt alerts the user to the possibility that the detected weight change may be due to factors (e.g. equipment) other than the patient's natural weight gain or weight loss.

In some cases, the weight threshold value is selected based on a minimum weight of typical medical equipment and/or or a maximum weight change expected for the patient based on a weighing schedule. Often, patients are weighed at least once per day, and so a patient's maximum expected weight gain or loss from day-to-day can be used to set the threshold value. Weight gains or losses that exceed the typical daily weight loss or gain of a person are flagged as possibly being due to equipment changes, whereas weight gains or losses that are less than this value are assumed to be due to patient weight gain or loss, and therefore are not flagged.

Non-patient weight from medical equipment, pillows, blankets etc. on the patient support apparatus 20 is indistinguishable from patient weight by the force sensors 54. If medical equipment or other sources of non-patient weight are added the patient support apparatus 20 after the tare weight is determined, and such weights are not entered into an equipment log, the weight readings will be too high and will not accurately reflect the patient's weight. Likewise, if medical equipment or other sources of non-patient weight were previously accounted for in the equipment log when saving the patient's weight, but have subsequently been removed from the litter frame without also removing them from the equipment log, the weight reading will also be too high and not valid. It can be critical to the care of a patient to closely monitor their weight, including tracking fluctuations in weight over time. Accordingly, patient support apparatus 20 is configured to allow the user to maintain a log of added and removed equipment, as well as to warn the user if there are weight changes that may reflect medical equipment or other objects being added or removed from patient support apparatus 20. With such warnings, the user is less likely to forget to update the equipment log when he or she adds equipment to, or removes equipment from, patient support apparatus 20. As noted, such warnings are issued, in at least one embodiment, based on a comparison of the current weight value, as determined based on reading from the force sensors 54, to the previously saved patient weight reading. If the weight change ($\Delta W$) is greater than the threshold value, controller 66 issues the warning to the user. If not, controller 66 accepts the weight change as being due to a change in the patient's actual weight.

Returning to scale home screen 122 of FIG. 7, if the user presses the "save weight" control 126, the controller 66 determines if the weight change $\Delta W$ (current gross weight minus tare weight minus any weight that is currently stored in the equipment log as compared to the previously stored patient weight) is greater or less than the predetermined threshold (e.g. ±2.0 kg). This is done at step 210. If the change in weight is less than the threshold, controller 66 saves the current weight reading (e.g. 55.5 kg in the example of FIG. 7) as the patient's weight. If the change in weight is greater than the threshold, controller 66 executes step 212 and displays either screen 156 of FIG. 12 or screen 156 of FIG. 13. More specifically, if the change in weight is an increase of more than the threshold, controller 66 displays screen 156 of FIG. 12, and if the change in weight is a decrease of more than the threshold, controller 66 displays screen 156 of FIG. 13. From screens 156 of FIG. 12 or 13, the user can press the save control 160, which saves the current weight reading as the patient's most recent weight, or the user can press the "cancel" icon 162, allowing themselves to make one or more adjustments to the equipment log prior to saving the patient's weight. Pressing the save control 160 corresponds to step 216 of algorithm 200.

Warning screens 156 of FIGS. 12 and 13 can be pop-up windows displayed over a portion of the scale home screen 122, such that the scale home screen 122 is still partially visible behind the pop-up window, or warning screens 156 may replace the scale home screen 122 entirely. Warning screens 156 include a warning message 158 notifying the user of the possible error in the weight reading, including text and/or graphics describing that there may have been a piece of equipment or other non-patient weight added to or removed from the apparatus 20. In the example of FIG. 12, the warning message 158 lets the user know that a piece of equipment may have been added to the bed. The warning message 158 also lets the user know that they have the option to save the weight reading anyway.

Each warning screen 156 also includes a save weight control 160 that allows the user to save the weight reading. This bypasses the need for the user to navigate to the scale home screen 122 to save the weight reading. Upon user-selection of the save weight control 160, the controller 66 is operable to store the current weight reading as the patient's weight. The gain/loss calculation is also updated and saved. After pressing the save weight control 160, the controller 66 displays scale home screen 122, shown in FIG. 7, on touchscreen 72. Optionally, after saving, a notification alerting the user of the save and/or the of gain/loss updates can be shown on the touchscreen 72 for a few seconds before reverting back to the screen 122 shown in FIG. 7.

Each warning screen 156 also includes a cancel control 162 that allows the user to return to the scale home screen 122 of FIG. 7 without saving the weight reading. Alternatively, instead of or in addition to the cancel icon 162, controller 66 can be configured to stop displaying warning screen 156 in response to a user touching the touchscreen 72 anywhere outside the boundaries of the screen 156 in those embodiments where the screen 156 is smaller than the display area of the touchscreen 72.

After a new reading of the patient's weight is saved, either in response to pressing the save weight control 126 of FIG. 7 or the save control 60 of FIG. 12 or 13, controller 66 updates the gain/loss indicator 132 (by initially resetting it to zero and subsequently adjusting it as changes occur with respect to the last saved patient weight reading).

The scale home screen 122 (FIGS. 7-11) also includes an equipment icon 140. Equipment icon 140 provides the user with an indication of whether an equipment weight log currently has any items stored in it or not. For example, if the equipment log is empty, equipment icon 140 may be displayed in a first color, and if it is not empty, it may be displayed in a second and different color. In addition to a color change indicating the use/non-use of the equipment weight log, equipment icon 140 (FIG. 7) also displays the total number of items in the weight log and the total weight of those items. This number depends on equipment being added and removed from the log properly, as described in further detail below, and helps user confidence with the displayed patient weight since the user can easily compare the displayed equipment number to the equipment he or she visually sees on patient support apparatus 20. When the equipment log is utilized by the user, it allows the user to separate out the weight of non-patient items from the patient's weight. As will be discussed more below, the user updates the equipment weight log by accessing an equipment log screen 142 (FIG. 14) and adding or removing equipment one piece at a time.

In order to make changes to the equipment log, the user presses on equipment icon 140, and in response thereto, controller 66 displays an equipment log screen 142, shown in FIG. 14, on touchscreen 72. This corresponds to steps 206 and 208 of algorithm 200. The display of equipment screen 142 may occur immediately after the equipment icon 140 is pressed, or there may be one or more intermediate controls/screens that need to be followed before getting to equipment screen 142. However arrived at, the display of equipment screen 142 includes an equipment weight indicator 144 that, in at least one embodiment, comprises a numeric value representing the total weight of the equipment that is stored within the equipment log. In other embodiments, equipment weight indicator 144 may indicate other values, such as the difference between the current sensed weight (minus the tare weight) and the value achieved after subtracting the equipment log weight from the last saved weight. Still other ways may be used to calculate weight indicator 144, which is not necessarily a true indication of the weight of the equipment, but rather may be an estimated or assumed weight of the equipment.

In the example of FIG. 14, weight indicator 144 corresponds to the total weight of the items in the equipment log and is shown to be zero because the equipment log is currently empty. Via the equipment screen 142, the user can manually add equipment weight or other non-patient weight to the equipment log. This is accomplished in the manner indicated by instruction message 148. That is, a user proceeds to screen 142, physically adds the first piece of equipment onto litter frame 28, allows it to rest there long enough for the scale system to detect the weight of the added equipment, and then presses the save icon 150. If the user wishes to add additional pieces of equipment, this procedure is repeated for separately for each piece of equipment that is added. As noted, once a piece of equipment is added to the equipment log, controller 66 is configured to take the logged equipment weight or other non-patient weight into account when calculating the patient's weight. More specifically, the total weight of the equipment in the log is subtracted by controller 66 from the gross weight readings of the scale system 56 (along with the tare weight) to arrive at the current patient weight. When equipment is removed from the log, controller 66 removes its corresponding weight from the log and performs the same calculation to determine the patient's weight. By subtracting the total weight of the equipment in the equipment log from the gross weight sensed (minus the tare weight), all non-patient weight on the support deck 30 that has been properly entered into the equipment log is accounted for, and the weight indicator 124 will consequently reflect an accurate patient weight that includes no non-patient weight components.

As noted, equipment screen 142 includes an instruction message 148 notifying the user of the necessary steps to enter equipment or other non-patient weight into the equipment log. The instruction message 148 can include text and/or graphics describing such steps. For example, the instruction message 148 can let the user know that: equipment can be added or removed now, one piece at a time. The instruction message 148 can additionally or alternatively include a warning, such as that new equipment should be removed from the support deck 30 and re-added (see the example of FIG. 18); or that old equipment was removed from the support deck 30 and should be re-added (see the example of FIG. 19). The particular message displayed depends upon whether the weight has increased or decreased by more than the threshold, as determined in step 220 of algorithm 200. Thus, controller 66 displays the message of FIG. 18 at step 222 if the weight has increased by more than the threshold, and controller 66 displays the message of FIG. 19 at step 222 if the weight has decreased by more than the threshold.

The equipment screen 142 includes a save equipment control 150 that allows the user to save the current equipment weight and number, as indicated by the equipment weight indicator 144 and the equipment number indicator 146. In response to user-selection of the save equipment control 150, the controller 66 is configured to store the current equipment weight and number in the equipment weight log. In an alternative embodiment, controller 66 may be programmed to automatically the save equipment control 150 on the equipment screen 142 after equipment is added or removed from the apparatus 20, i.e. after the scale system 56 detects a weight change. When no equipment is logged, as shown in FIG. 14, the save equipment control 150 is disabled.

The equipment screen 142 includes a reset control 152 that allows the user to cancel all added or removed equipment, i.e. to reset both the equipment weight and equipment number to zero in the equipment weight log. The reset control 152 provides the user with a convenient way to reset equipment weight through the software implemented by the controller 66. Reset control 152 therefore provides a one-touch quick option for cancelling all of the contents of the equipment log.

In response to user-selection of the reset control 152, the controller 66 may prompt the user to confirm the reset before proceeding. Optionally, the controller 66 enables the reset control 152 on the equipment screen 142 after equipment is added or removed from the apparatus 20, i.e. after the scale system 56 detects a weight change. When no equipment is logged, as shown in FIG. 14, the reset control 152 is disabled.

The equipment screen 142 includes a return control 154 that allows the user to return to the scale home screen 122. After user-selection of the return control 154, the controller 66 is operable to display the scale home screen 122. If equipment changes have been made but not saved, i.e. by pressing the save equipment control 150, upon pressing the return control 154, the user can be prompted to save the changes before leaving the equipment screen 142. Pressing the return control 154 corresponds to step 228 of algorithm 200.

Figure 15:
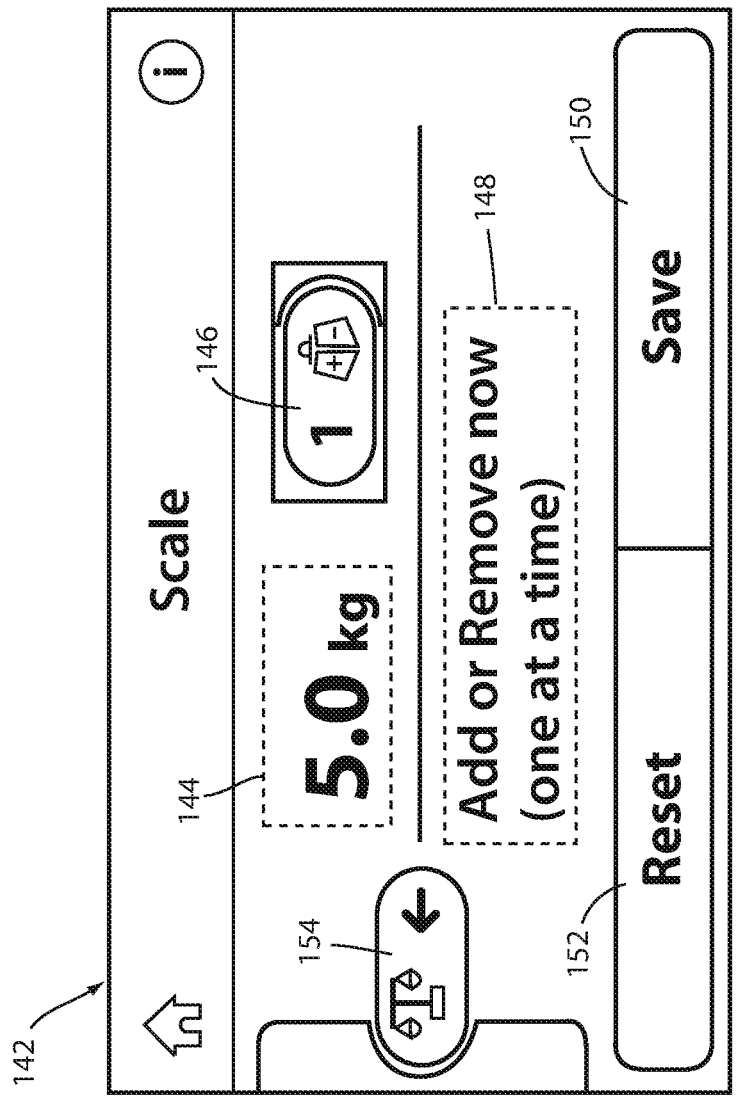
FIG. 15 is the equipment screen of FIG. 14 after a first piece of equipment has been manually added to an equipment weight log of the patient support apparatus.

FIG. 15 shows the equipment screen 142 after a first piece of equipment has been manually added to the equipment log of patient support apparatus 20 by the user. In this example, the user has added an item weighing 5.0 kg to the apparatus 20, the equipment weight indicator 144 has been updated to show a total equipment weight of 5.0 kg, and the equipment number indicator 146 has been updated to show the total pieces of equipment on the apparatus 20 as one. Also as shown in FIG. 15, the reset icon 152 is enabled because the weight log is not empty, and a user is therefore able to reset this log to zero (the reset icon 152 may be ghosted, or otherwise inactivated when the weight log is zero).

In some embodiments, controller 66 displays the save icon 150 in a ghosted manner if controller 66 does not detect any change in weight since the equipment screen 142 was initially displayed. That is, in at least one embodiment, controller 66 displays a value for weight indicator 166 that reflects the change in sensed weight, if any, between the moment screen 142 was initially displayed and the current moment. Thus, for example, when the user brings up screen 142 (such as by pressing equipment icon 140 in FIG. 7), controller 66 initially displays a zero value for weight indicator 166 when screen 142 is first displayed. From that point forward, if the force sensors 54 detect any changes in weight, controller 66 displays that changed weight in indicator 144. As a result, when the user wishes to add, say, a four kilogram piece of equipment, indicator 144 will initially appear as zero when screen 142 is first displayed, and then will change to four kilograms once the user adds the piece of equipment to the litter frame 28. At that point, because controller 66 has sensed a non-zero change in weight since initially displaying screen 142, controller 66 will enable the save icon 150. The enablement of save icon 150 may be indicated in a variety of ways, such as by changing it from a ghosted appearance when inactive to a non-ghosted appearance when active, by some other type of color change, by removing it completely when inactive, or by still other visual techniques.

Continuing with the aforementioned example further, once the user has added the four kilogram piece of equipment and controller 66 is displaying a value of four kilograms at indicator 144, the user presses the save icon 150 to enter the equipment into the equipment log. Once it is saved and entered, the user has the option of continuing to use screen 142 to enter additional weight into the equipment log. In at least one embodiment controller 66 is configured to continue to display the weight of the first piece of equipment summed together with any second piece of equipment that is added to the litter frame 28 in indicator 144. Thus, if a user adds a second piece of equipment weighing three kilograms to the litter frame 28, controller 66 updates indicator 144 to show a value of seven kilograms, which corresponds to the sum of both pieces of equipment.

In another alternative embodiment, once a first piece of equipment is entered into the equipment log, controller 66 immediately resets the value shown in indicator 144 to zero and thereafter only displays the value of any changes in weight that occur since the first piece of equipment was added and saved to the log. In this modified embodiment, if a user adds a second piece of equipment after entering the first piece of equipment into the log, controller 66 displays the weight of only the second piece of equipment at indicator 144 (rather than the combined weight of both pieces of equipment).

Figure 16:
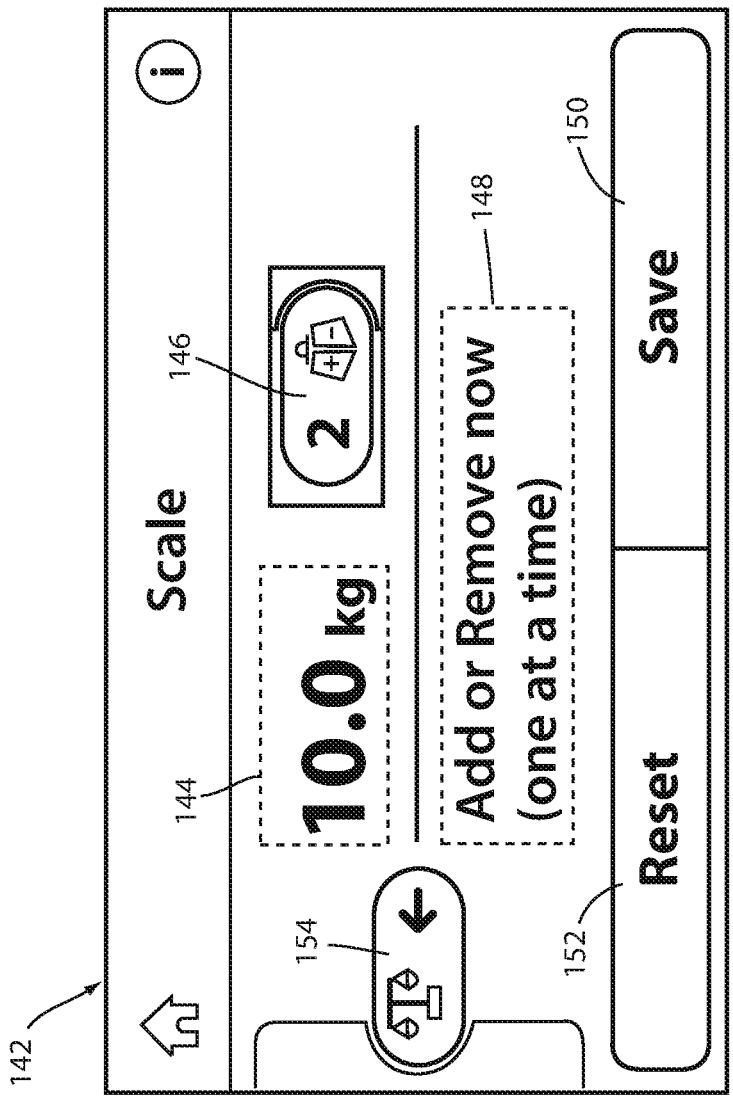
FIG. 16 is the equipment screen of FIG. 14 after a second piece of equipment has been manually added to the equipment weight log of the patient support apparatus.
Figure 17:
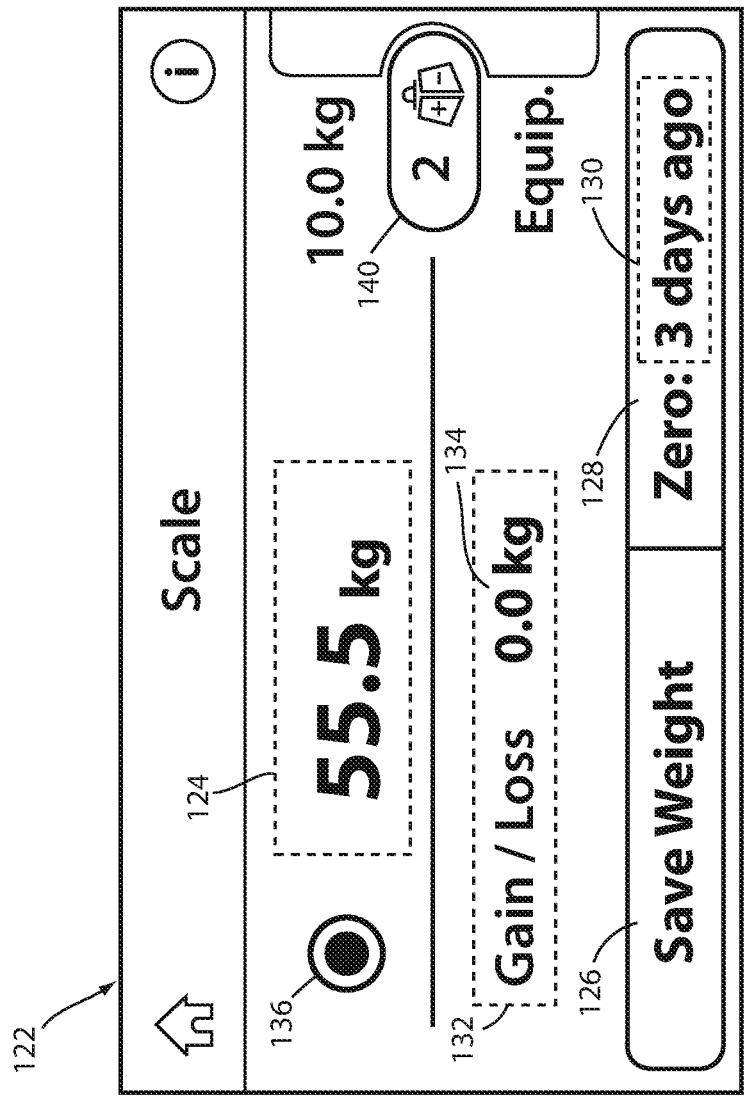
FIG. 17 is the scale screen of FIG. 14 modified to show that the equipment weight log has been populated by the user with two pieces of equipment.

FIG. 16 shows an example of the equipment screen 142 after a second piece of equipment has been added to the equipment log by the user. In this example, the equipment weight indicator 144 has been updated to show a total equipment weight of 10.0 kg, and the equipment number indicator 146 has been updated to show the total pieces of equipment on the apparatus 20 as two. Also as shown in FIG. 16 the save and reset icons 150, 152 remain enabled.

After the user has manually added and saved all equipment or other non-patient weight added to the patient support apparatus 20, the user can return to the scale home screen 122 by pressing the return control 154. The scale home screen 122 will be displayed in an updated fashion to reflect the changes made to the equipment log. Thus, for example, if the user has changed the equipment log such that two items are stored therein weighing a total of ten kilograms, controller 66 will display an updated scale home screen 122 like that shown in FIG. 17. As can be seen therein when compared to the scale home screen 122 of FIG. 7, the equipment icon 140 has been updated with the number "2" to indicate two items are in the weight log, and has also been updated with the text "10.0 kg," which corresponds to the total weight of the items in the equipment log. If the result of the changes made to the equipment log is an empty equipment log, controller 66 will display a scale home screen 122 of the type shown in FIG. 7.

As was noted above with respect to algorithm 200 (FIG. 6), before controller 66 allows a user to add or remove an item form the equipment weight log, it performs a check at step 220 to see if the current weight reading has changed by more than the threshold (which may be indicative of the user having prematurely added the equipment to the litter frame 28 or prematurely removed the equipment from litter frame 28). Further, as noted above if, if the check indicates that the weight has changed by more than the threshold, controller 66 is configured to display a warning screen, such as shown in the examples of FIG. 18 and FIG. 19. More specifically, if the weight change is an increase in weight that is greater than the threshold, controller 66 is configured to display a warning such as that shown in FIG. 18, and if the weight change is a decrease in weight that is greater than the threshold, controller 66 is configured to display a warning such as that shown in FIG. 19.

In the warning screen of FIG. 18, the warning message 148 instructs the user to take what is presumed to be new equipment off of the litter frame 28 and re-add it. This forces the user to manually remove the equipment and re-add it to the litter frame, thereby giving controller 66 the opportunity to monitor the precise weight change that occurs in response to the addition of the equipment (and thus to obtain an accurate reading of the weight of the equipment). Once the item is removed and re-added, the save icon 150 becomes active and the user can press it, thereby adding the piece of equipment to the equipment log. Alternatively, once controller 66 detects that the item has been removed and re-added, it may automatically add the piece of equipment to the log, thereby enabling the user to simply lift and drop the equipment in order for it to get entered into the weight log.

In the warning screen of FIG. 19, the warning message 148 instructs the user to replace what is presumed to have been previously removed equipment back on the litter frame and then remove it. This forces the user to manually add the equipment back to the litter frame, thereby giving controller 66 the opportunity to monitor the precise weight change that occurs in response to the removal of the equipment (and thus to obtain an accurate reading of the weight of the removed equipment). Once the equipment is re-added and subsequently removed, the save icon 150 becomes active and the user can press it, thereby removing the piece of equipment from the weight log.

As noted previously, the warning message 148 of FIGS. 18 and 19 serve to provide notice to the user that he or she may have added or removed equipment prior to controller 66 being ready to add or remove it from the weight log. The screens of FIGS. 18 and 19 therefore help ensure that the user notifies controller 66 of weight changes due to equipment addition or removal.

It is noted that, for the scale home screen 122, the weight indicator 124, the gain/loss indicator 134, and the gain/loss information icon 136 dynamically update as weight is added to or removed from the patient support apparatus 20, as determined by the scale system 56 via the force sensors 54.

Therefore, when a patient is in the apparatus 20, a live, up-to-date patient weight and gain/loss calculations are shown on the screen 122. The scale home screen 122 can therefore immediately indicate to the user changes in patient weight.

Figure 20:
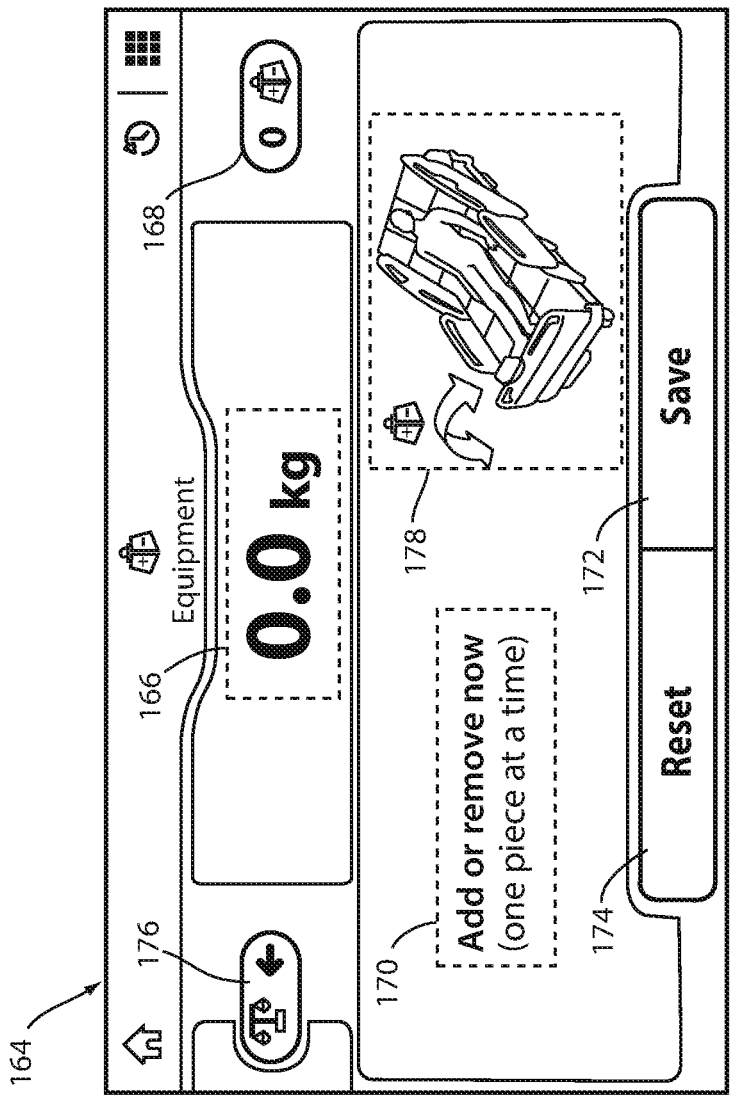
FIG. 20 is another embodiment of an illustrative equipment screen that may be displayed on the touchscreen of FIG. 5 in lieu of the screen of FIG. 14 when a user wishes to add weight to, or remove weight from, the equipment weight log maintained by the patient support apparatus.

FIG. 20 shows an alternative embodiment of an equipment addition/removal screen that may be displayed on the touchscreen of FIG. 5 in lieu of the equipment screen 142 of FIG. 14. Upon user-selection of the equipment icon 140 on any of the scale screens 122 described previously, the controller 66 displays a scale equipment screen 164, shown in FIG. 20, on touchscreen 72. The display of equipment screen 164 may occur immediately after the equipment icon 140 is pressed, or there may be one or more intermediate controls/screens that need to be followed before getting to equipment screen 164. However arrived at, the display of equipment screen 164 includes an equipment weight indicator 166 comprising a numeric value representing the total weight of equipment added to the equipment log, as determined by the scale/exit detection system 56, i.e. the force sensors 54, and an equipment number indicator 168 comprising a numeric value representing the total number of pieces of equipment in the equipment log. Via the equipment screen 164, the user can manually log equipment weight or other non-patient weight added or removed from the patient support apparatus 20.

The equipment screen 164 also includes an instruction message 170, a save equipment control 172, a reset control 174, and a return control 176 which can operate as described previously for controls 150, 154, and 154 of the equipment screen 142. The equipment screen 164 also includes a graphic 178 accompanying the instruction message 170 that provides the user with a visual indication of the necessary steps needed to log equipment or other non-patient weight. In the present embodiment, the graphic 178 shows a weight being added to the patient support apparatus 20, with a patient on the apparatus 20. Other graphics 178 are possible, including static or animated graphics. Audible instructions can also be issued from a speaker associate with the user interface 62.

To the extent not already described, the different content and functions of the various control screens of patient support apparatus 20, including the various embodiments of the scale home screen and the equipment screens disclosed herein, may be used in combination with each other as desired, and/or the content and/or functions of one control screen may be applied to one or more other control screen. Further, the selected content shown in any particular control screen herein is not to be construed that it must have all of the content shown therein.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a litter frame;
a support deck supported on the litter frame and adapted to support a patient thereon;
a plurality of force sensors adapted to output signals corresponding to downward forces exerted on the support deck;
a display; and
a controller in operative communication with the plurality of force sensors and the display, the controller configured to display on the display an equipment weight indicator comprising a first numeric value representing a total weight of equipment added to or removed from the support deck and entered into a weight log and a patient weight indicator comprising a second numeric value representative of a current patient weight of the patient supported by the support deck based on readings from the plurality of force sensors;
wherein the controller is adapted to characterize the second numeric value as being an accurate patient weight or as possibly including non-patient weight not yet entered into the weight log, and to display a warning message if the second numeric value is characterized as possibly including non-patient weight not yet entered into the weight log.

2. The patient support apparatus of claim 1, wherein the controller is configured to determine the second numeric value by subtracting the first numeric value representing the total weight of equipment added to or removed from the support deck from a gross weight detected by the plurality of force sensors.

3. The patient support apparatus of claim 1, wherein the controller is configured to determine the second numeric value by subtracting a tare weight and the first numeric value representing the total weight of equipment added to or removed from the support deck from a gross weight detected by the plurality of force sensors.

4. The patient support apparatus of claim 1, wherein the controller is further adapted to display a scale equipment screen comprising an instruction message notifying a user of the steps to log equipment or other non-patient weight, the instruction message comprising instructions to at least one of: add equipment to the patient support apparatus; remove equipment from the patient support apparatus; take new equipment off of the patient support apparatus; or reset the scale equipment screen.

5. The patient support apparatus of claim 1, wherein the controller is further adapted to display an information icon comprising an indication of whether the current patient weight of the patient has increased, decreased, or has not changed since last weighing the patient; and wherein the controller is configured to display an arrow for the information icon when the current patient weight of the patient has increased or decreased.

6. The patient support apparatus of claim 1, wherein the controller is further adapted to display a gain/loss indicator comprising a third numeric value representative of a difference between the current patient weight and a previously saved weight of the patient; wherein the controller is configured to compare the third numeric value to a weight change threshold and display the warning message if the weight change threshold is exceeded.

7. A patient support apparatus comprising:
a litter frame;
a support deck supported on the litter frame and adapted to support a patient thereon;
a plurality of force sensors adapted to output signals corresponding to downward forces exerted on the support deck;
a display;
a controller in communication with the plurality of force sensors, the controller configured to:
receive the signals provided by the plurality of force sensors;
analyze the signals to determine a weight of a load supported on the support deck;
maintain a weight log of non-patient weight added to, or removed from, the support deck;
subtract a total weight of the weight log from the weight of the load to determine a potential patient weight;
characterize the potential patient weight as being an accurate patient weight or as possibly including non-patient weight not yet entered into the weight log;
display a scale home screen including a save weight control and a weight indicator comprising a numeric value representative of the potential patient weight; and
upon user-selection of the save weight control on the scale home screen, display a warning screen comprising a warning message if the potential patient weight is characterized as possibly including non-patient weight not yet entered into the weight log.

8. The patient support apparatus of claim 7, wherein the scale home screen comprises an information icon comprising an indication of whether the weight of the load supported on the support deck has increased, decreased, or has not changed since last weighing the patient.

9. The patient support apparatus of claim 7, wherein the controller is configured to subtract a tare weight from the weight of the load to determine the potential patient weight.

10. The patient support apparatus of claim 7, wherein the warning message comprises an indicator that a piece of equipment may have been removed from the patient support apparatus or added to the patient support apparatus.

11. The patient support apparatus of claim 7, wherein the warning screen comprises a save icon allowing a user to save the potential patient weight as a current patient weight without accessing the scale home screen; wherein, after user-selection of the save icon on the warning screen, the controller is operable to display the scale home screen; and wherein the warning screen comprises a cancel icon and the controller is configured to display the cancel icon simultaneously with the save icon, the cancel icon allowing the user to return to the scale home screen without saving the potential patient weight as the current patient weight.

12. The patient support apparatus of claim 7, wherein the scale home screen comprises a zero control and after user-selection of the zero control, the controller is operable to establish a tare weight; wherein the zero control comprises an indication of when the tare weight was last saved; wherein the controller determines the potential patient weight by also subtracting the tare weight from the weight of the load; and wherein the scale home screen comprises an equipment icon displaying the total weight of the weight log.

13. The patient support apparatus of claim 7, wherein the scale home screen comprises a gain/loss indicator representative of a difference between the potential patient weight and a previously saved weight of the patient; and wherein the controller is configured characterize the potential patient weight as possibly including non-patient weight if the difference exceeds a weight change threshold.

14. A patient support apparatus comprising:
a litter frame;
a support deck supported on the litter frame and adapted to support a patient thereon;
a plurality of force sensors adapted to output signals corresponding to downward forces exerted on the support deck;
a display;
a controller in communication with the plurality of force sensors, the controller configured to:
receive the signals provided by the plurality of force sensors;
analyze the signals to determine a weight of a load supported on the support deck and characterize the weight as being an accurate patient weight or as possibly including non-patient weight not yet entered into a weight log;
display a scale home screen including:
a save weight control;
an equipment icon including a first numeric value representing a total weight of equipment added to or removed from the support deck and entered into the weight log, and a second numeric value representing a total number of pieces of equipment on the support deck and entered into the weight log; and
a weight indicator comprising a third numeric value representative of the weight; and
upon user-selection of the equipment icon on the scale home screen, display a scale equipment screen comprising an equipment weight indicator comprising the first numeric value and an equipment number indicator comprising the second numeric value; and
upon user-selection of the save weight control on the scale home screen, display a warning screen comprising a warning message if the weight is characterized as possibly including non-patient weight not yet entered into the weight log.

15. The patient support apparatus of claim 14, wherein the controller is configured dynamically update the first numeric value of the equipment weight indicator on the scale equipment screen as weight is added to or removed from the support deck, as determined by the plurality of force sensors; and wherein the controller is also configured dynamically update the third numeric value on the scale home screen as weight is added to or removed from the support deck, as determined by the plurality of force sensors.

16. The patient support apparatus of claim 14, wherein the controller is configured to determine the third numeric value by subtracting a tare weight and the first numeric value representing the total weight of equipment added to or removed from the support deck from a gross weight detected by the plurality of force sensors.

17. The patient support apparatus of claim 14, wherein the scale equipment screen comprises an instruction message, the instruction message including at least one of the following: a notification to a user of the steps to log equipment or other non-patient weight into the weight log; instructions to add equipment to the patient support apparatus; instructions to remove equipment from the patient support apparatus; instructions to take new equipment off of the patient support apparatus; instructions to reset the scale equipment screen; a warning that equipment may have been added to the patient support apparatus without entering the equipment into the weight log; or a warning that equipment may have been removed from the patient support apparatus without removing the equipment from the weight log.

18. The patient support apparatus of claim 14, wherein the controller is configured to compare a difference between the weight and a previously saved weight of the patient to a weight change threshold, characterize the weight as being an accurate patient weight if the difference does not exceed the weight change threshold, and characterize the weight as possibly including non-patient weight not yet entered into the weight log if the difference exceeds the weight change threshold, and wherein the warning message comprises an indicator that a piece of equipment may have been removed from the patient support apparatus or added to the patient support apparatus.

19. The patient support apparatus of claim 18 wherein the weight is determined by subtracting a tare weight and the first numeric value from the weight of the load.

* * * * *